US012788515B2

(12) United States Patent
Begum et al.

(10) Patent No.: US 12,788,515 B2
(45) Date of Patent: Nov. 10, 2026

(54) SURGICAL ROBOTIC SYSTEM AND METHOD FOR LAPAROSCOPIC INSTRUMENTS AND CAMERA NAVIGATION

(71) Applicant: Covidien LP, Mansfield, MA (US)

(72) Inventors: Fathima Begum, Hyderabad (IN); Seshanaveen Posani, Hyderabad (IN); Sanket Anil Nawate, Pune (IN); Jyothi Sheela Bonthu, Hyderabad (IN); K V S Manoj Kumar Vadali, Hyderabad (IN)

(73) Assignee: Covidien LP, Mansfield, MA (US)

( * ) Notice: Subject to any disclaimer, the term of this patent is extended or adjusted under 35 U.S.C. 154(b) by 176 days.

(21) Appl. No.: 18/760,267

(22) Filed: Jul. 1, 2024

(65) Prior Publication Data

US 2025/0041007 A1 Feb. 6, 2025

Related U.S. Application Data

(60) Provisional application No. 63/517,158, filed on Aug. 2, 2023.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/25* (2016.02); *A61B 90/361* (2016.02); *A61B 2034/2057* (2016.02)

(58) Field of Classification Search
CPC .................. A61B 34/25; A61B 90/361; A61B 2034/2057; A61B 34/20; A61B 2090/364;
(Continued)

(56) References Cited

U.S. PATENT DOCUMENTS 6,132,368 A 10/2000 Cooper
6,206,903 B1 3/2001 Ramans
(Continued)

OTHER PUBLICATIONS

Extended European Search Report issued in corresponding application EP 24 19 2287.1 dated Jan. 22, 2025 (8 pages).

*Primary Examiner* — Jonathan T Kuo
(74) *Attorney, Agent, or Firm* — Carter, DeLuca & Farrell, LLP

(57) ABSTRACT

A surgical robotic system includes a surgical robotic arm having a surgical device and an instrument drive unit configured to actuate the surgical device. The system also includes a surgeon console configured to receive user input to control at least one of the surgical robotic arm or the surgical device. The system further includes a control tower coupled to the surgical robotic arm and the surgeon console. The control tower includes a storage device and a controller configured to store a plurality of checkpoints on the storage device. Each checkpoint of the plurality of checkpoints includes image data of a surgical site and position data corresponding to a prior position of the surgical robotic arm during a surgical procedure. The controller is also configured to output a graphical user interface (GUI) on a display screen. The GUI is configured to display the image data of at least one checkpoint of the plurality of checkpoints and to receive user input selecting the checkpoint. The controller is further configured to control the surgical robotic arm to move the surgical robotic arm to the prior position based on the selected checkpoint.

20 Claims, 22 Drawing Sheets

(51) Int. Cl.
*A61B 34/20* (2016.01)
*A61B 90/00* (2016.01)

(58) Field of Classification Search
CPC .............. A61B 2090/365; A61B 90/37; A61B 2034/2059; A61B 2034/2065; A61B 34/74; A61B 34/76; A61B 2034/252; A61B 2034/302; A61B 2034/742; A61B 34/30–34/37
See application file for complete search history.

(56) References Cited

U.S. PATENT DOCUMENTS

| | | | |
|---|---|---|---|
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,926,709 | B2 | 8/2005 | Bieger et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |

(56) References Cited

U.S. PATENT DOCUMENTS

| | | | |
|---|---|---|---|
| 8,668,638 B2 | 3/2014 | Donhowe et al. | |
| 8,746,252 B2 | 6/2014 | McGrogan et al. | |
| 8,749,189 B2 | 6/2014 | Nowlin et al. | |
| 8,749,190 B2 | 6/2014 | Nowlin et al. | |
| 8,758,352 B2 | 6/2014 | Cooper et al. | |
| 8,761,930 B2 | 6/2014 | Nixon | |
| 8,768,516 B2 | 7/2014 | Diolaiti et al. | |
| 8,786,241 B2 | 7/2014 | Nowlin et al. | |
| 8,790,243 B2 | 7/2014 | Cooper et al. | |
| 8,808,164 B2 | 8/2014 | Hoffman et al. | |
| 8,816,628 B2 | 8/2014 | Nowlin et al. | |
| 8,821,480 B2 | 9/2014 | Burbank | |
| 8,823,308 B2 | 9/2014 | Nowlin et al. | |
| 8,827,989 B2 | 9/2014 | Niemeyer | |
| 8,838,270 B2 | 9/2014 | Druke et al. | |
| 8,852,174 B2 | 10/2014 | Burbank | |
| 8,858,547 B2 | 10/2014 | Brogna | |
| 8,862,268 B2 | 10/2014 | Robinson et al. | |
| 8,864,751 B2 | 10/2014 | Prisco et al. | |
| 8,864,752 B2 | 10/2014 | Diolaiti et al. | |
| 8,903,546 B2 | 12/2014 | Diolaiti et al. | |
| 8,903,549 B2 | 12/2014 | Itkowitz et al. | |
| 8,911,428 B2 | 12/2014 | Cooper et al. | |
| 8,912,746 B2 | 12/2014 | Reid et al. | |
| 8,944,070 B2 | 2/2015 | Guthart | |
| 8,989,903 B2 | 3/2015 | Weir et al. | |
| 9,002,518 B2 | 4/2015 | Manzo | |
| 9,014,856 B2 | 4/2015 | Manzo et al. | |
| 9,016,540 B2 | 4/2015 | Whitman et al. | |
| 9,019,345 B2 | 4/2015 | O'Grady et al. | |
| 9,043,027 B2 | 5/2015 | Durant et al. | |
| 9,050,120 B2 | 6/2015 | Swarup et al. | |
| 9,055,961 B2 | 6/2015 | Manzo et al. | |
| 9,068,628 B2 | 6/2015 | Solomon et al. | |
| 9,078,684 B2 | 7/2015 | Williams | |
| 9,084,623 B2 | 7/2015 | Gomez et al. | |
| 9,095,362 B2 | 8/2015 | Dachs, II et al. | |
| 9,096,033 B2 | 8/2015 | Holop et al. | |
| 9,101,381 B2 | 8/2015 | Burbank et al. | |
| 9,113,877 B1 | 8/2015 | Whitman et al. | |
| 9,138,284 B2 | 9/2015 | Krom et al. | |
| 9,144,456 B2 | 9/2015 | Rosa et al. | |
| 9,198,730 B2 | 12/2015 | Prisco et al. | |
| 9,204,923 B2 | 12/2015 | Manzo et al. | |
| 9,226,648 B2 | 1/2016 | Saadat et al. | |
| 9,226,750 B2 | 1/2016 | Weir et al. | |
| 9,226,761 B2 | 1/2016 | Burbank | |
| 9,232,984 B2 | 1/2016 | Guthart et al. | |
| 9,241,766 B2 | 1/2016 | Duque et al. | |
| 9,241,767 B2 | 1/2016 | Prisco et al. | |
| 9,241,769 B2 | 1/2016 | Larkin et al. | |
| 9,259,275 B2 | 2/2016 | Burbank | |
| 9,259,277 B2 | 2/2016 | Rogers et al. | |
| 9,259,281 B2 | 2/2016 | Griffiths et al. | |
| 9,259,282 B2 | 2/2016 | Azizian et al. | |
| 9,261,172 B2 | 2/2016 | Solomon et al. | |
| 9,265,567 B2 | 2/2016 | Orban, III et al. | |
| 9,265,584 B2 | 2/2016 | Itkowitz et al. | |
| 9,283,049 B2 | 3/2016 | Diolaiti et al. | |
| 9,301,811 B2 | 4/2016 | Goldberg et al. | |
| 9,314,307 B2 | 4/2016 | Richmond et al. | |
| 9,317,651 B2 | 4/2016 | Nixon | |
| 9,345,546 B2 | 5/2016 | Toth et al. | |
| 9,393,017 B2 | 7/2016 | Flanagan et al. | |
| 9,402,689 B2 | 8/2016 | Prisco et al. | |
| 9,417,621 B2 | 8/2016 | Diolaiti | |
| 9,424,303 B2 | 8/2016 | Hoffman et al. | |
| 9,433,418 B2 | 9/2016 | Whitman et al. | |
| 9,439,556 B2 | 9/2016 | Pandya et al. | |
| 9,446,517 B2 | 9/2016 | Burns et al. | |
| 9,452,020 B2 | 9/2016 | Griffiths et al. | |
| 9,474,569 B2 | 10/2016 | Manzo et al. | |
| 9,480,533 B2 | 11/2016 | Devengenzo et al. | |
| 9,503,713 B2 | 11/2016 | Zhao et al. | |
| 9,550,300 B2 | 1/2017 | Danitz et al. | |
| 9,554,859 B2 | 1/2017 | Nowlin et al. | |
| 9,566,124 B2 | 2/2017 | Prisco et al. | |
| 9,579,164 B2 | 2/2017 | Itkowitz et al. | |
| 9,585,641 B2 | 3/2017 | Cooper et al. | |
| 9,615,883 B2 | 4/2017 | Schena et al. | |
| 9,623,563 B2 | 4/2017 | Nixon | |
| 9,623,902 B2 | 4/2017 | Griffiths et al. | |
| 9,629,520 B2 | 4/2017 | Diolaiti | |
| 9,662,177 B2 | 5/2017 | Weir et al. | |
| 9,664,262 B2 | 5/2017 | Donlon et al. | |
| 9,675,354 B2 | 6/2017 | Weir et al. | |
| 9,687,312 B2 | 6/2017 | Dachs, II et al. | |
| 9,700,334 B2 | 7/2017 | Hinman et al. | |
| 9,718,190 B2 | 8/2017 | Larkin et al. | |
| 9,730,719 B2 | 8/2017 | Brisson et al. | |
| 9,737,199 B2 | 8/2017 | Pistor et al. | |
| 9,795,446 B2 | 10/2017 | DiMaio et al. | |
| 9,797,484 B2 | 10/2017 | Solomon et al. | |
| 9,801,690 B2 | 10/2017 | Larkin et al. | |
| 9,814,530 B2 | 11/2017 | Weir et al. | |
| 9,814,536 B2 | 11/2017 | Goldberg et al. | |
| 9,814,537 B2 | 11/2017 | Itkowitz et al. | |
| 9,820,823 B2 | 11/2017 | Richmond et al. | |
| 9,827,059 B2 | 11/2017 | Robinson et al. | |
| 9,830,371 B2 | 11/2017 | Hoffman et al. | |
| 9,839,481 B2 | 12/2017 | Blumenkranz et al. | |
| 9,839,487 B2 | 12/2017 | Dachs, II | |
| 9,850,994 B2 | 12/2017 | Schena | |
| 9,855,102 B2 | 1/2018 | Blumenkranz | |
| 9,855,107 B2 | 1/2018 | Labonville et al. | |
| 9,872,737 B2 | 1/2018 | Nixon | |
| 9,877,718 B2 | 1/2018 | Weir et al. | |
| 9,883,920 B2 | 2/2018 | Blumenkranz | |
| 9,888,974 B2 | 2/2018 | Niemeyer | |
| 9,895,813 B2 | 2/2018 | Blumenkranz et al. | |
| 9,901,408 B2 | 2/2018 | Larkin | |
| 9,918,800 B2 | 3/2018 | Itkowitz et al. | |
| 9,925,013 B2 * | 3/2018 | Dell | A61B 90/361 |
| 9,943,375 B2 | 4/2018 | Blumenkranz et al. | |
| 9,948,852 B2 | 4/2018 | Lilagan et al. | |
| 9,949,798 B2 | 4/2018 | Weir | |
| 9,949,802 B2 | 4/2018 | Cooper | |
| 9,952,107 B2 | 4/2018 | Blumenkranz et al. | |
| 9,956,044 B2 | 5/2018 | Gomez et al. | |
| 9,980,778 B2 | 5/2018 | Ohline et al. | |
| 10,008,017 B2 | 6/2018 | Itkowitz et al. | |
| 10,028,793 B2 | 7/2018 | Griffiths et al. | |
| 10,033,308 B2 | 7/2018 | Chaghajerdi et al. | |
| 10,034,719 B2 | 7/2018 | Richmond et al. | |
| 10,052,167 B2 | 8/2018 | Au et al. | |
| 10,085,811 B2 | 10/2018 | Weir et al. | |
| 10,092,165 B2 | 10/2018 | Power | |
| 10,092,344 B2 | 10/2018 | Mohr et al. | |
| 10,123,844 B2 | 11/2018 | Nowlin | |
| 10,188,471 B2 | 1/2019 | Brisson | |
| 10,201,390 B2 | 2/2019 | Swarup et al. | |
| 10,213,202 B2 | 2/2019 | Flanagan et al. | |
| 10,258,416 B2 | 4/2019 | Mintz et al. | |
| 10,278,782 B2 | 5/2019 | Jarc et al. | |
| 10,278,783 B2 | 5/2019 | Itkowitz et al. | |
| 10,282,881 B2 | 5/2019 | Itkowitz et al. | |
| 10,335,242 B2 | 7/2019 | Devengenzo et al. | |
| 10,398,521 B2 | 9/2019 | Itkowitz et al. | |
| 10,405,934 B2 | 9/2019 | Prisco et al. | |
| 10,433,922 B2 | 10/2019 | Itkowitz et al. | |
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |

(56) References Cited

U.S. PATENT DOCUMENTS

| | | | |
|---|---|---|---|
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,917,543 | B2 * | 2/2021 | Ramirez Luna ....... B25J 9/0009 |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 11,376,002 | B2 | 7/2022 | Shelton, IV et al. |
| 11,376,098 | B2 | 7/2022 | Shelton, IV et al. |
| 11,381,759 | B2 | 7/2022 | Zhao et al. |
| 11,382,621 | B2 | 7/2022 | Scheib et al. |
| 11,382,624 | B2 | 7/2022 | Harris et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,638 | B2 | 7/2022 | Harris et al. |
| 11,382,644 | B2 | 7/2022 | Schoettgen et al. |
| 11,389,160 | B2 | 7/2022 | Shelton, IV et al. |
| 11,389,255 | B2 | 7/2022 | DiMaio et al. |
| 11,399,906 | B2 | 8/2022 | Shelton, IV et al. |
| 11,406,379 | B2 | 8/2022 | Hess et al. |
| 11,410,259 | B2 | 8/2022 | Harris et al. |
| 11,419,630 | B2 | 8/2022 | Yates et al. |
| 11,424,027 | B2 | 8/2022 | Shelton, IV |
| 11,432,888 | B2 | 9/2022 | Diolaiti et al. |
| 11,432,893 | B2 | 9/2022 | Itkowitz et al. |
| 11,432,895 | B2 | 9/2022 | Loh et al. |
| 11,439,390 | B2 | 9/2022 | Patel et al. |
| 11,439,391 | B2 | 9/2022 | Bruns et al. |
| 11,468,791 | B2 | 10/2022 | Jarc et al. |
| 11,471,155 | B2 | 10/2022 | Shelton, IV et al. |
| 11,471,221 | B2 | 10/2022 | Zhao et al. |
| 11,478,308 | B2 | 10/2022 | Hoffman et al. |
| 11,490,977 | B2 | 11/2022 | Schena et al. |
| 11,497,499 | B2 | 11/2022 | Shelton, IV et al. |
| 11,504,119 | B2 | 11/2022 | Shelton, IV et al. |
| 11,504,124 | B2 | 11/2022 | Patel et al. |
| 11,510,743 | B2 | 11/2022 | Shelton, IV et al. |
| 11,517,312 | B2 | 12/2022 | Wixey |
| 11,517,325 | B2 | 12/2022 | Shelton, IV et al. |
| 11,518,048 | B2 | 12/2022 | Saraliev et al. |
| 12,307,581 | B2 * | 5/2025 | Moller .................... G06T 15/20 |
| 2007/0198008 | A1 * | 8/2007 | Hauck .................. A61B 5/6885 606/41 |
| 2016/0070436 | A1 | 3/2016 | Thomas et al. |
| 2017/0202628 | A1 * | 7/2017 | Dell ....................... A61B 34/30 |
| 2019/0005848 | A1 | 1/2019 | Garcia Kilroy et al. |
| 2019/0327394 | A1 * | 10/2019 | Ramirez Luna ....... A61B 34/77 |
| 2020/0345451 | A1 | 11/2020 | Peine et al. |
| 2021/0393339 | A1 | 12/2021 | Johnson et al. |
| 2022/0020160 | A1 | 1/2022 | Buharin |
| 2022/0104887 | A1 * | 4/2022 | Hufford ................. A61B 34/25 |
| 2023/0099522 | A1 * | 3/2023 | Moller .................... G06T 19/00 345/419 |
| 2023/0190394 | A1 | 6/2023 | Tam et al. |
| 2025/0195166 | A1 * | 6/2025 | Peine ..................... A61B 34/35 |

* cited by examiner

FIG. 17
200
Procedure ID
000000
3 Large Needle Driver
4 Scope 30°
2 Double Fenestrated Grasper
1 Cadiere Forceps
System Warning: High priority system alarms will appear here in alarm red and can truncate if necessary. [DISMISS]
System Warning: Low or medium priority system alarms will appear here in alarm yellow and can truncate if necessary. [DISMISS]
Dynamic Checkpoints
Save Checkpoint
208a
01:56
02:01
202e
208c
208b

SURGICAL ROBOTIC SYSTEM AND METHOD FOR LAPAROSCOPIC INSTRUMENTS AND CAMERA NAVIGATION

CROSS-REFERENCE TO RELATED APPLICATIONS

This application claims the benefit of, and priority to, U.S. Provisional Patent Application Ser. No. 63/517,158 filed on Aug. 2, 2023. The entire contents of the foregoing application is incorporated by reference herein.

BACKGROUND

Surgical robotic systems are currently being used in a variety of surgical procedures, including minimally invasive surgical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body. A laparoscopic camera, which is also held by one of the robotic arms, is inserted into the patient to image the surgical site. During the robotic surgical procedure, doctors continuously monitor a surgeon display screen disposed on the surgeon console and guide the camera to the anatomy of interest in stepwise manner as the surgeon is navigating around other ports and their respective instruments. As a result, the instruments and camera may be moved multiple times (e.g., hundreds). This process makes robotic surgery complex and time-consuming. Furthermore, the camera may get fogged and must be removed from the patient cavity to be cleaned and replaced at the same position. Placing and removing the camera requires multiple movement steps that surgeon needs to retrace. Multiple movements of the instruments and camera not only increase the procedure duration but also increase the anesthesia dose required for patient, which in turn, increases the recovery duration and cost of procedure.

SUMMARY

The present disclosure provides a surgical robotic system that is configured to store navigation position checkpoints of a laparoscopic camera as well as navigation position checkpoints of one or more instruments inserted into the patient. The checkpoints may be saved manually and/or automatically. The system provides a user interface for the surgeon and the staff, which may be used to save the positions of the instruments and the camera. The user interface may also be used to retract the camera and the instruments at any time during the surgical procedure such that the system automatically moves the camera and/or the instruments to the selected checkpoint.

In one embodiment, the checkpoint process may be used for extraction (e.g., for cleaning) and reinsertion. In this embodiment, an initial position of the camera while it is out of the patient cavity is recorded as a first checkpoint. A robotic arm then inserts the camera into the patient body to perform the surgical procedure. If the camera fogs up, the surgeon can recall the camera to its initial position (i.e., the first checkpoint). One or more subsequent checkpoints for camera position may be also recorded after the insertion to generate a so-called breadcrumb navigation trail along which the system can automatically navigate the camera, in either the backward or forward direction. Thus, once the camera cleaning is completed, the surgeon can recall the latest checkpoint position, so that the arm will move automatically to a desired (e.g., the last known) recorded position automatically. The same navigation trails may be used for insertion and navigation of instruments. The term "trail" denotes the path formed using the co-ordinates of instruments or camera saved during the procedure.

The checkpoint system may also be used to restore the system after a power failure or from a serious error in the system. In case of power failure, an emergency battery backup may not allow surgeon to operate the arms. The checkpoints may be created for each of the robotic arms and instruments allowing for an automated restoration process.

According to one embodiment of the present disclosure, a surgical robotic system is disclosed. The surgical robotic system includes a surgical robotic arm having a surgical device and an instrument drive unit configured to actuate the surgical device. The system also includes a surgeon console configured to receive user input to control at least one of the surgical robotic arm or the surgical device. The system further includes a control tower coupled to the surgical robotic arm and the surgeon console. The control tower includes a storage device and a controller configured to store a plurality of checkpoints on the storage device. Each checkpoint of the plurality of checkpoints includes image data of a surgical site and position data corresponding to a prior position of the surgical robotic arm during a surgical procedure. The controller is also configured to output a graphical user interface (GUI) on a display screen. The GUI is configured to display the image data of at least one checkpoint of the plurality of checkpoints and to receive user input selecting the checkpoint. The controller is further configured to control the surgical robotic arm to move the surgical robotic arm to the prior position based on the selected checkpoint.

Implementations of the above embodiment may include one or more of the following features. According to one aspect of the above embodiment, the controller may be further configured to store the checkpoint in response to activation of the surgical device. The controller may be also configured to store the checkpoint in response to a user command. The controller may be additionally configured to store the checkpoint based on an elapsed time of the surgical procedure. The controller may be further configured to detect a phase of the surgical procedure. The controller may be also configured to store the checkpoint based on the detected phase of the surgical procedure. The surgical device may be a surgical robotic instrument or a laparoscopic camera. The checkpoint may include the position data corresponding to the laparoscopic camera being outside a patient.

According to another embodiment of the present disclosure, a method for restoring positional state of a surgical robotic system is disclosed. The method includes storing on a storage device a plurality of checkpoints including image data of a surgical site and position data corresponding to a prior position during a surgical procedure of a laparoscopic camera held by a surgical robotic arm. A first checkpoint corresponds to a position of the laparoscopic camera being outside a patient and a second checkpoint of the plurality of checkpoints corresponds to a position of the laparoscopic camera being inside patient. The method further includes outputting a graphical user interface (GUI) configured to display on a display screen the image data of the plurality of checkpoints. The method additionally includes receiving a first user input through the GUI selecting the at least one of the first checkpoint or the second checkpoint and controlling the surgical robotic arm to move the surgical robotic arm to the prior position based on selection of at least one of the first checkpoint or the second checkpoint.

Implementations of the above embodiment may include one or more of the following features. According to one aspect of the above embodiment, the method may further include storing the first checkpoint or the second checkpoint in response to activation of the laparoscopic camera. The method may further include storing the first checkpoint or the second checkpoint in response to a user command. The method may additionally include storing the first checkpoint or the second checkpoint based on an elapsed time of the surgical procedure. The method may also include detecting a phase of the surgical procedure; and storing the first checkpoint or the second checkpoint based on the detected phase of the surgical procedure.

According to a further embodiment of the present disclosure, a method for restoring positional state of a surgical robotic system is disclosed. The method includes storing a plurality of checkpoints on a storage device. Each checkpoint of the plurality of checkpoints includes image data of a surgical site and position data corresponding to a prior position of a surgical robotic arm during a surgical procedure. The method further includes outputting a graphical user interface (GUI) configured to display on a display screen the image data of at least one checkpoint of the plurality of checkpoints. The method additionally includes receiving user input through the GUI selecting the at least one checkpoint and controlling the surgical robotic arm to move the surgical robotic arm to the prior position based on the selected at least one checkpoint.

Implementations of the above embodiment may include one or more of the following features. According to one aspect of the above embodiment, the method may also include storing the checkpoint in response to activation of a surgical device held by the surgical robotic arm. The method may also include storing the checkpoint in response to a user command. The method may additionally include storing the checkpoint based on an elapsed time of the surgical procedure. The method may also include detecting a phase of the surgical procedure and storing the checkpoint based on the detected phase of the surgical procedure.

BRIEF DESCRIPTION OF THE DRAWINGS

Various embodiments of the present disclosure are described herein with reference to the drawings wherein.

DETAILED DESCRIPTION

Figure 1:
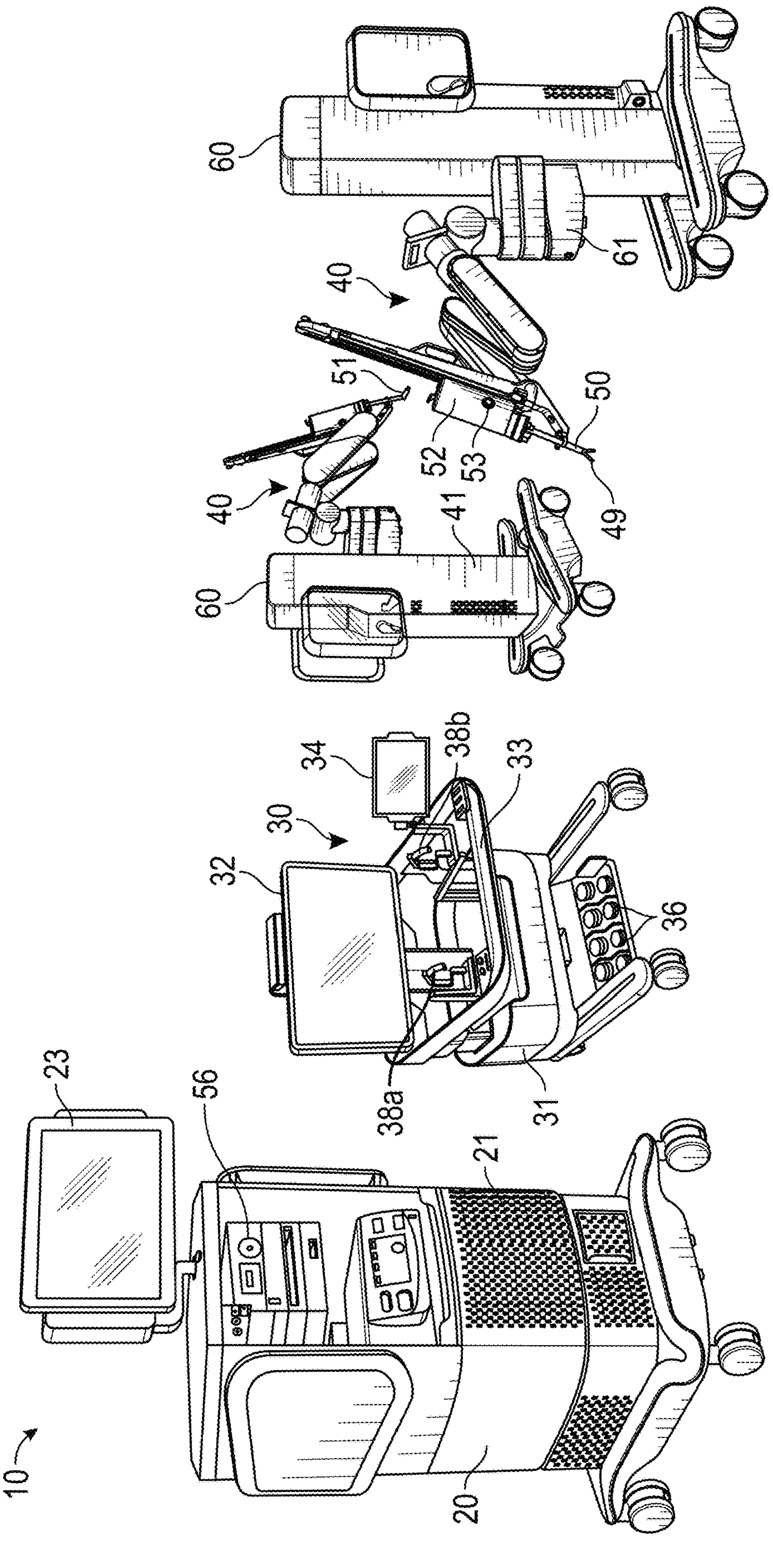
FIG. 1 is a perspective view of a surgical robotic system including a control tower, a console, and one or more surgical robotic arms each disposed on a mobile cart according to an embodiment of the present disclosure.

Embodiments of the presently disclosed surgical robotic system are described in detail with reference to the drawings, in which like reference numerals designate identical or corresponding elements in each of the several views.

With reference to FIG. 1, a surgical robotic system 10 includes a control tower 20, which is connected to all the components of the surgical robotic system 10 including a surgeon console 30 and one or more mobile carts 60. Each of the mobile carts 60 includes a robotic arm 40 having a surgical instrument 50 removably coupled thereto. The robotic arms 40 also couple to the mobile carts 60. The robotic system 10 may include any number of mobile carts 60 and/or robotic arms 40.

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

One of the robotic arms 40 may include a laparoscopic camera 51 configured to capture video of the surgical site. The laparoscopic camera 51 may be a stereoscopic camera configured to capture two side-by-side (i.e., left and right) images of the surgical site to produce a video stream of the surgical scene. The laparoscopic camera 51 is coupled to an image processing device 56, which may be disposed within the control tower 20. The image processing device 56 may be any computing device configured to receive the video feed from the laparoscopic camera 51 and output the processed video stream.

The surgeon console 30 includes a first screen 32, which displays a video feed of the surgical site provided by camera 51 of the surgical instrument 50 disposed on the robotic arm 40, and a second screen 34, which displays a user interface for controlling the surgical robotic system 10. The first screen 32 and second screen 34 may be touchscreens allowing for displaying various graphical user inputs.

The surgeon console 30 also includes a plurality of user interface devices, such as foot pedals 36 and a pair of hand controllers 38*a* and 38*b* which are used by a user to remotely control robotic arms 40. The surgeon console further includes an armrest 33 used to support clinician's arms while operating the hand controllers 38*a* and 38*b*.

The control tower 20 includes a screen 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the hand controllers 38*a* and 38*b*. The foot pedals 36 may be used to enable and lock the hand controllers 38*a* and 38*b*, repositioning camera movement and electrosurgical activation/deactivation. In particular, the foot pedals 36 may be used to perform a clutching action on the hand controllers 38*a* and 38*b*. Clutching is initiated by pressing one of the foot pedals 36, which disconnects (i.e., prevents movement inputs) the hand controllers 38*a* and/or 38*b* from the robotic arm 40 and corresponding instrument 50 or camera 51 attached thereto. This allows the user to reposition the hand controllers 38*a* and 38*b* without moving the robotic arm(s) 40 and the instrument 50 and/or camera 51. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DC). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
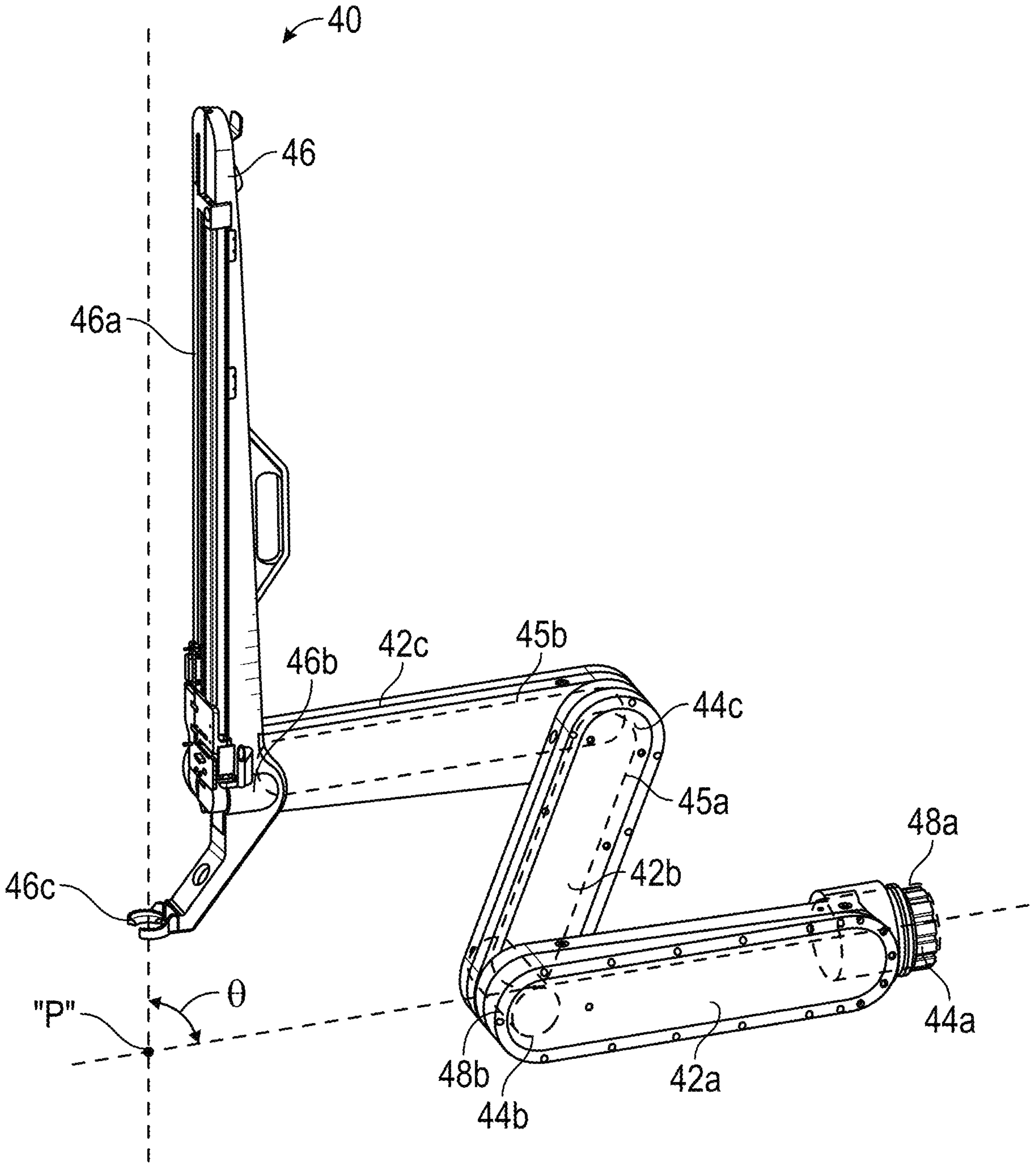
FIG. 2 is a perspective view of a surgical robotic arm of the surgical robotic system of FIG. 1 according to an embodiment of the present disclosure.
Figure 3:
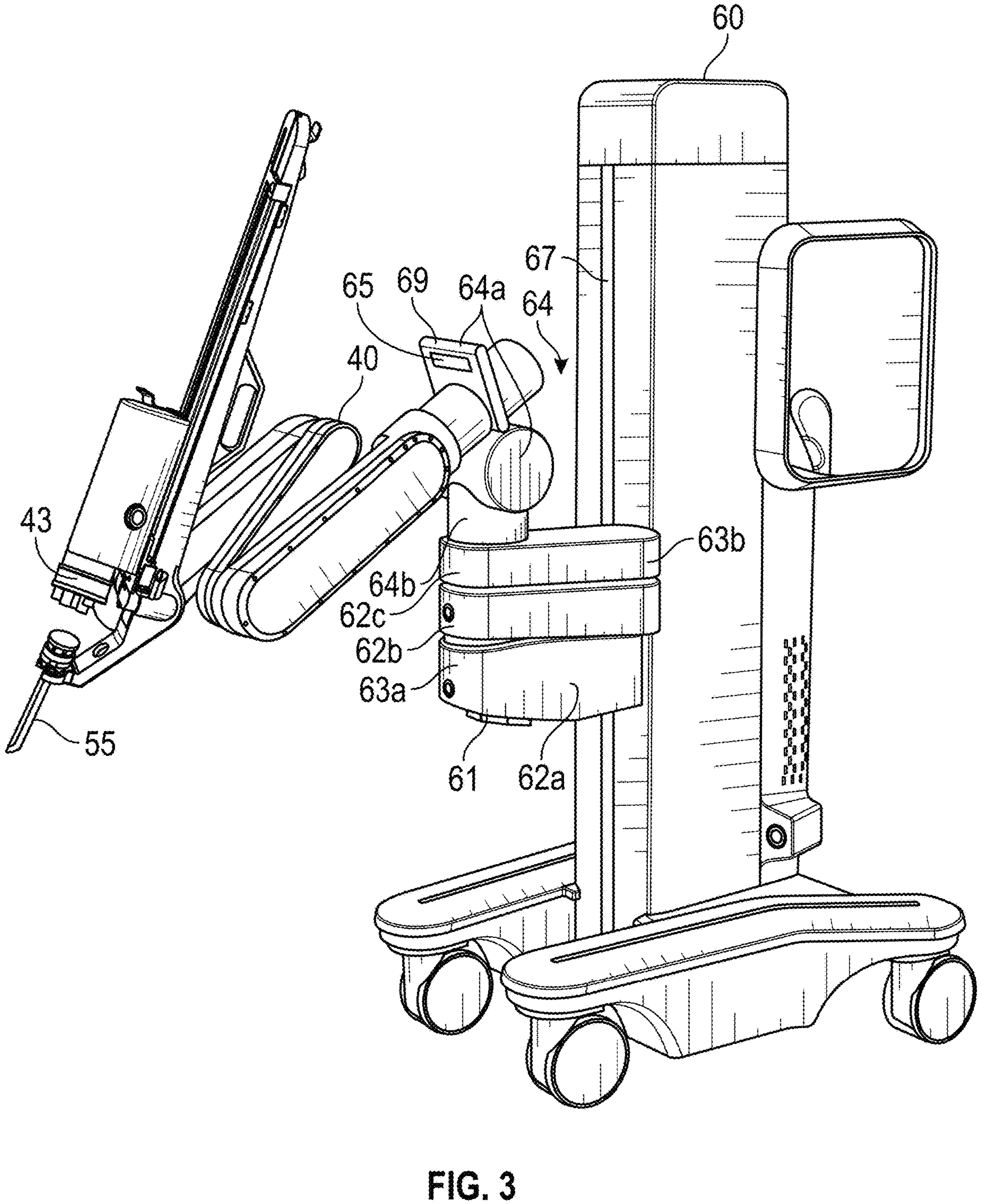
FIG. 3 is a perspective view of a mobile cart having a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. Other configurations of links and joints may be utilized as known by those skilled in the art. The joint 44*a* is configured to secure the robotic arm 40 to the mobile cart 60 and defines a first longitudinal axis. With reference to FIG. 3, the mobile cart 60 includes a lift 67 and a setup arm 61, which provides a base for mounting the robotic arm 40. The lift 67 allows for vertical movement of the setup arm 61. The mobile cart 60 also includes a screen 69 for displaying information pertaining to the robotic arm 40. In embodiments, the robotic arm 40 may include any type and/or number of joints.

The setup arm 61 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62*a*, 62*b*, 62*c* as well as the lift 67. In embodiments, the setup arm 61 may include any type and/or number of joints.

The third link 62*c* may include a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and a holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle $\theta$ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted to achieve the desired angle $\theta$. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components an end effector 49 of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During laparoscopic procedures, the instrument 50 may be inserted through a laparoscopic access port 55 (FIG. 3) held by the holder 46. The holder 46 also includes a port latch 46*c* for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
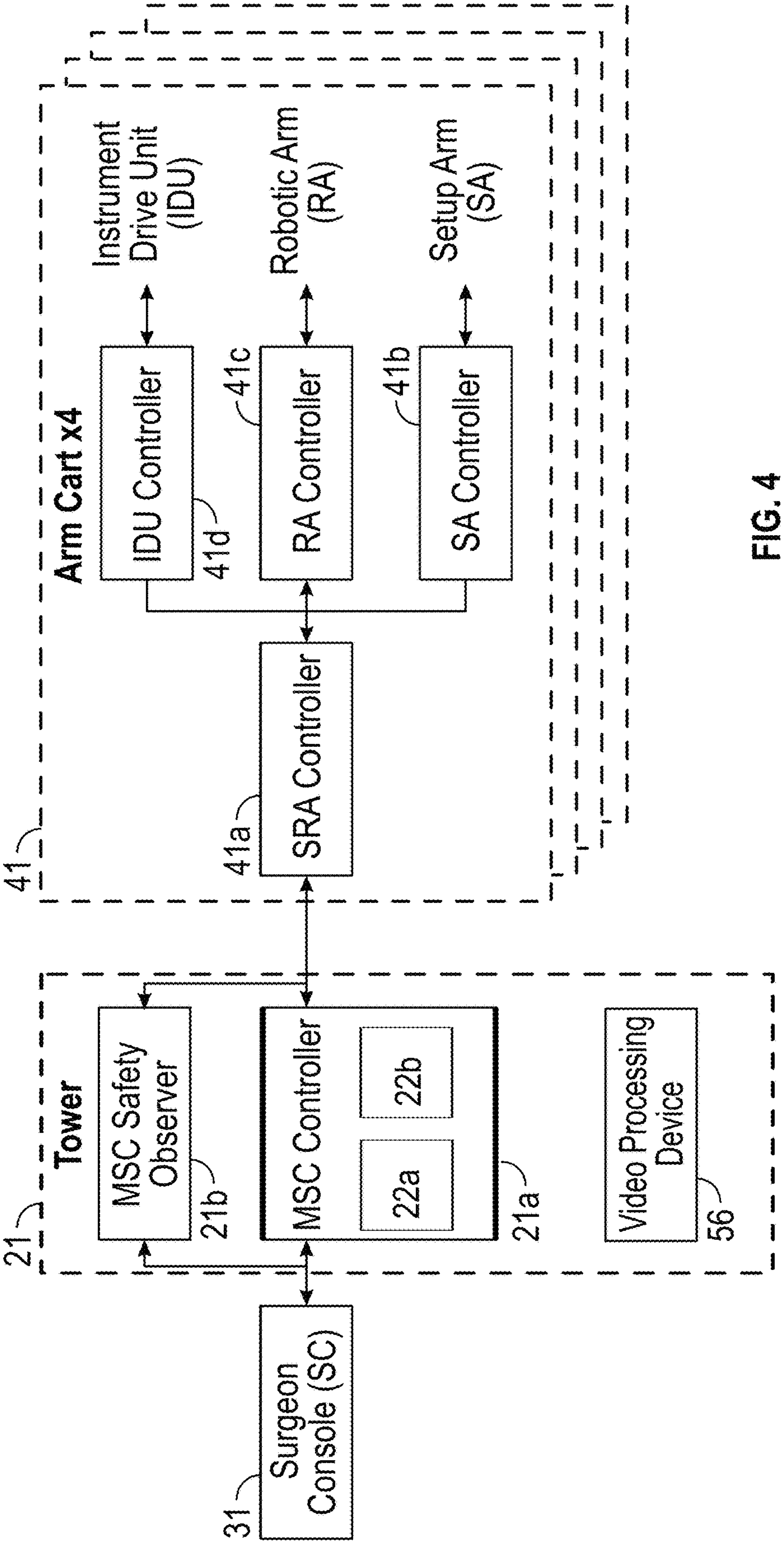
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the hand controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the hand controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The controller 21*a* is coupled to a storage 22*a*, which may be non-transitory computer-readable medium configured to store any suitable computer data, such as software instructions executable by the controller 21*a*. The controller 21*a* also includes transitory memory 22*b* for loading instructions and other computer readable data during execution of the instructions. In embodiments, other controllers of the system 10 include similar configurations.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the mobile cart 60, the robotic arm 40, and the IDU 52. The main cart controller 41*a* also communicates actual joint angles back to the controller 21*a*.

Each of joints 63*a* and 63*b* and the rotatable base 64 of the setup arm 61 are passive joints (i.e., no actuators are present therein) allowing for manual adjustment thereof by a user. The joints 63*a* and 63*b* and the rotatable base 64 include brakes that are disengaged by the user to configure the setup arm 61. The setup arm controller 41*b* monitors slippage of each of joints 63*a* and 63*b* and the rotatable base 64 of the setup arm 61, when brakes are engaged or can be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

Figure 5:
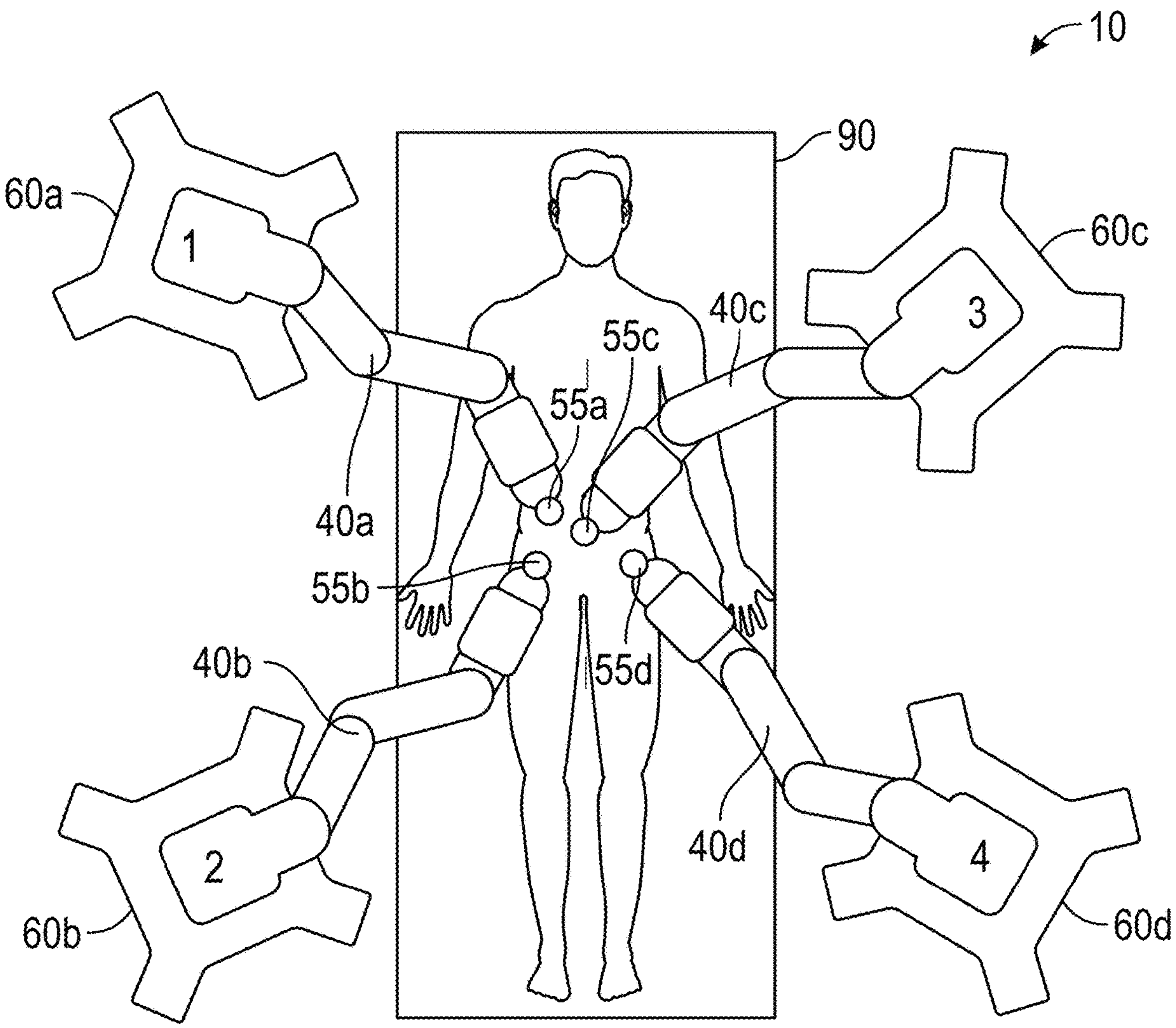
FIG. 5 is a plan schematic view of the surgical robotic system of FIG. 1 positioned about a surgical table according to an embodiment of the present disclosure.

With reference to FIG. 5, the surgical robotic system 10 is set up around a surgical table 90. The system 10 includes mobile carts 60*a-d*, which may be numbered "1" through "4." During setup, each of the carts 60*a-d* are positioned around the surgical table 90. Position and orientation of the carts 60*a-d* depends on a plurality of factors, such as placement of a plurality of access ports 55*a-d*, which in turn, depends on the surgery being performed. Once the port placement is determined, the access ports 55*a-d* are inserted into the patient, and carts 60*a-d* are positioned to insert instruments 50 and the laparoscopic camera 51 into corresponding ports 55*a-d*.

During use, each of the robotic arms 40*a-d* is attached to one of the access ports 55*a-d* that is inserted into the patient by attaching the latch 46*c* (FIG. 2) to the access port 55 (FIG. 3). The IDU 52 is attached to the holder 46, followed by the SIM 43 being attached to a distal portion of the IDU 52. Thereafter, the instrument 50 is attached to the SIM 43. The instrument 50 is then inserted through the access port 55 by moving the IDU 52 along the holder 46. The SIM 43 includes a plurality of drive shafts configured to transmit rotation of individual motors of the IDU 52 to the instrument 50 thereby actuating the instrument 50. In addition, the SIM 43 provides a sterile barrier between the instrument 50 and the other components of robotic arm 40, including the IDU 52. The SIM 43 is also configured to secure a sterile drape (not shown) to the IDU 52.

A surgical procedure may include multiple phases, and each phase may include one or more surgical actions. As used herein, the term "phase" represents a surgical event that is composed of a series of steps (e.g., closure). A "surgical action" may include an incision, a compression, a stapling, a clipping, a suturing, a cauterization, a scaling, or any other such actions performed to complete a phase in the surgical procedure. A "step" refers to the completion of a named surgical objective (e.g., hemostasis). During each step, certain surgical instruments 50 (e.g., forceps) are used to achieve a specific objective by performing one or more surgical actions.

Figure 6:
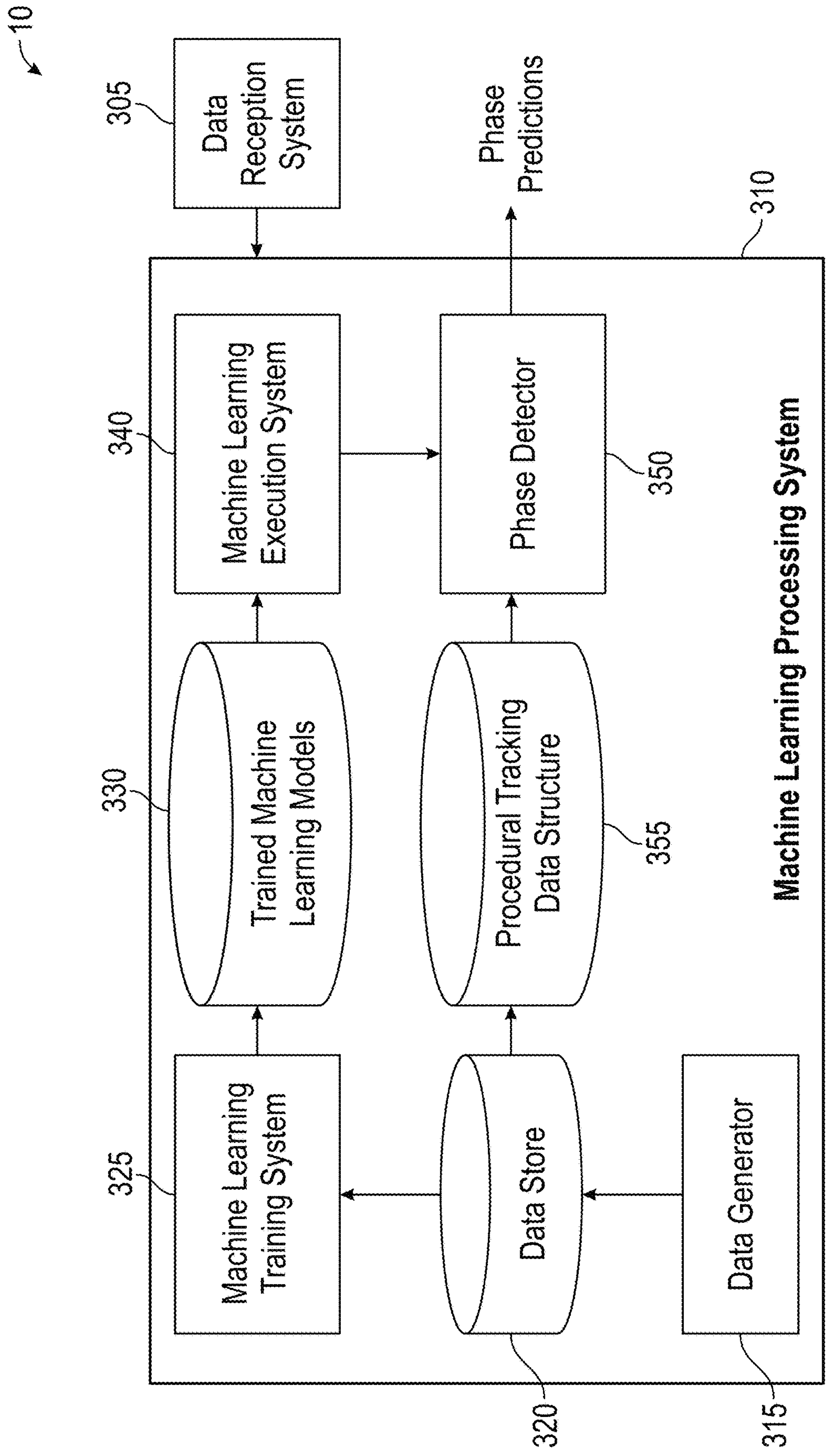
FIG. 6 is a schematic diagram of a system for determining phases of a surgical procedure according to an embodiment of the present disclosure.

With reference to FIG. 6, the surgical robotic system 10 may include a machine learning (ML) processing system 310 that processes the surgical data using one or more ML models to identify one or more features, such as surgical phase, instrument, anatomical structure, etc., in the surgical data. The ML processing system 310 includes a ML training system 325, which may be a separate device (e.g., server) that stores its output as one or more trained ML models 330. The ML models 330 are accessible by a ML execution system 340. The ML execution system 340 may be separate from the ML training system 325, namely, devices that "train" the models are separate from devices that "infer," i.e., perform real-time processing of surgical data using the trained ML models 330.

System 10 includes a data reception system 305 that collects surgical data, including the video data and surgical instrumentation data. The data reception system 305 can include one or more devices (e.g., one or more user devices and/or servers) located within and/or associated with a surgical operating room and/or control center. The data reception system 305 can receive surgical data in real-time, i.e., as the surgical procedure is being performed.

The ML processing system 310, in some examples, may further include a data generator 315 to generate simulated surgical data, such as a set of virtual images, or record the video data from the video processing device 56, to train the ML models 330 as well as other sources of data, e.g., user input, arm movement, etc. Data generator 315 can access (read/write) a data store 320 to record data, including multiple images and/or multiple videos.

The ML processing system 310 also includes a phase detector 350 that uses the ML models to identify a phase within the surgical procedure. Phase detector 350 uses a particular procedural tracking data structure 355 from a list of procedural tracking data structures. Phase detector 350 selects the procedural tracking data structure 355 based on the type of surgical procedure that is being performed. In one or more examples, the type of surgical procedure is predetermined or input by user. The procedural tracking data structure 355 identifies a set of potential phases that may correspond to a part of the specific type of surgical procedure.

In some examples, the procedural tracking data structure 355 may be a graph that includes a set of nodes and a set of edges, with each node corresponding to a potential phase. The edges may provide directional connections between nodes that indicate (via the direction) an expected order during which the phases will be encountered throughout an iteration of the surgical procedure. The procedural tracking data structure 355 may include one or more branching nodes that feed to multiple next nodes and/or may include one or more points of divergence and/or convergence between the nodes. In some instances, a phase indicates a procedural action (e.g., surgical action) that is being performed or has been performed and/or indicates a combination of actions that have been performed. In some instances, a phase relates to a biological state of a patient undergoing a surgical procedure. For example, the biological state may indicate a complication (e.g., blood clots, clogged arteries/veins, etc.), pre-condition (e.g., lesions, polyps, etc.). In some examples, the ML models 330 are trained to detect an "abnormal condition," such as hemorrhaging, arrhythmias, blood vessel abnormality, etc.

The phase detector 350 outputs the phase prediction associated with a portion of the video data that is analyzed by the ML processing system 310. The phase prediction is associated with the portion of the video data by identifying a start time and an end time of the portion of the video that is analyzed by the ML execution system 340. The phase prediction that is output may include an identity of a surgical phase as detected by the phase detector 350 based on the output of the ML execution system 340. Further, the phase prediction, in one or more examples, may include identities of the structures (e.g., instrument, anatomy, etc.) that are identified by the ML execution system 340 in the portion of the video that is analyzed. The phase prediction may also include a confidence score of the prediction. Other examples may include various other types of information in the phase prediction that is output. The predicted phase may be used by the controller 21*a* to determine when to implement the collision detection method described below.

Figure 7:
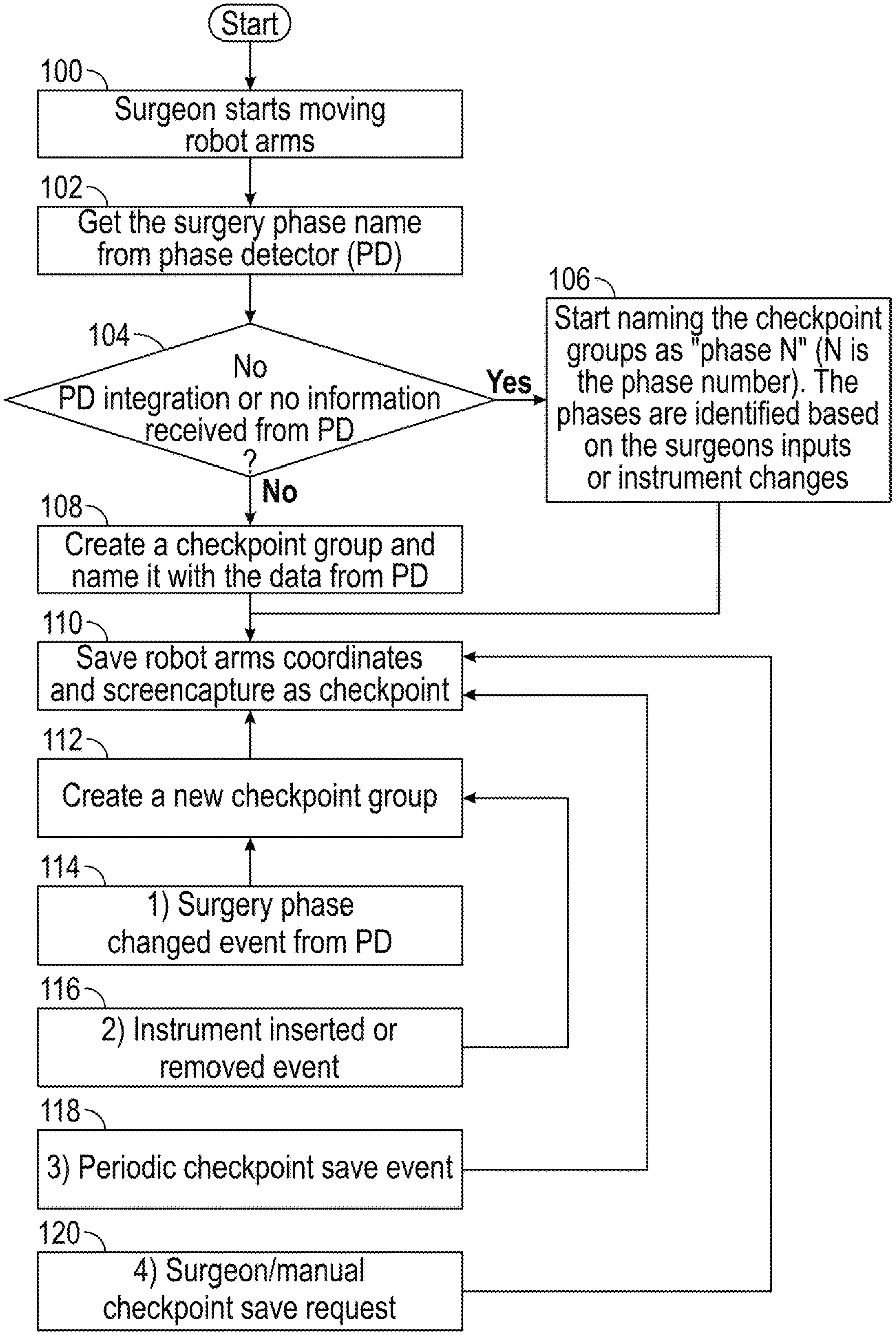
FIG. 7 is a flow chart of a method for saving checkpoints according to an embodiment of the present disclosure.

FIG. 7 shows a method for saving checkpoints for the robotic arm 40 controlling the camera 51. The method may be implemented as software instructions executable by the controller 21*a* or any other suitable processor of the system 10. While the method is described with respect to the moving of the camera 51 to saved checkpoints and its corresponding robotic arm 40, the method may be also extended to control other robotic arms 40 and their instruments 50.

With reference to FIG. 7, the method is implemented to be executed during operation of the system 10, i.e., during the surgical procedure. At step 100 the controller 21*a* determines that a surgeon operating the robotic arms 40, i.e., by detecting movement, paddle, or button presses at one or both of the handle controllers 38*a* and 38*b*. At step 102, the controller 21*a* attempts to obtain the surgery phase name from the phase detector 350. At step 104, if no information is received, e.g., if the phase detector 350 is not present or there is no corresponding phase available, the controller 21*a* proceeds to step 106 to enable manual naming of phases. The surgeon or any other user may identify and name a checkpoint group by entering, e.g., speech input, typing, etc. the phase name or another identifier. The checkpoint group organizes one or more checkpoints based on their phase.

If the phase detector 350 is active and was able to identify the current phase, then the controller 21*a* uses the current phase to a create a check point group at step 108. At step 110, a check point is generated and saved in storage 22*a* as part of the check point group. Each checkpoint includes data describing orientation and position of the robotic arms 40, e.g., coordinates in a world frame, joint angles, arm height, angle relative to the table 90, etc. Checkpoint also includes positional information for the IDU 52, e.g., angular motor position for one or more motors controlling the camera 51 and/or the instrument 50. The checkpoint also includes image data for the checkpoint, such as video taken during checkpoint creation and/or still images, such as screenshot (e.g., thumbnail) from the video. At step 112, the checkpoints may also be saved as part of a new checkpoint group, i.e., checkpoints that occur during a specific phase of the procedure.

The checkpoints may be generated and stored automatically as in step 114, based on detection of a specific phase. In particular, at step 116 the checkpoint is generated in response to insertion or removal of the camera 51 and the instruments 50 into the access ports 50*a-d*. Another automatic checkpoint generation routine may be done at step 118, which includes creating checkpoints after a set time period has elapsed, which may be done periodically, e.g., every minute. In addition to automatic checkpoint generation, the user may also do so manually at step 120 by commanding the surgeon console 30 to generate a checkpoint via a GUI 200 of FIGS. 9-20. In particular, FIG. 12 shows the GUI 200 including buttons 203*a* and 203*b*, which are used to generate manual checkpoints and to save a checkpoint manually, respectively. The system 10 may also continuously record and store checkpoints in a dynamic continuous manner, such that the user can choose to configure or restore the system 10 to any prior point in the surgical procedure.

Figure 8A:
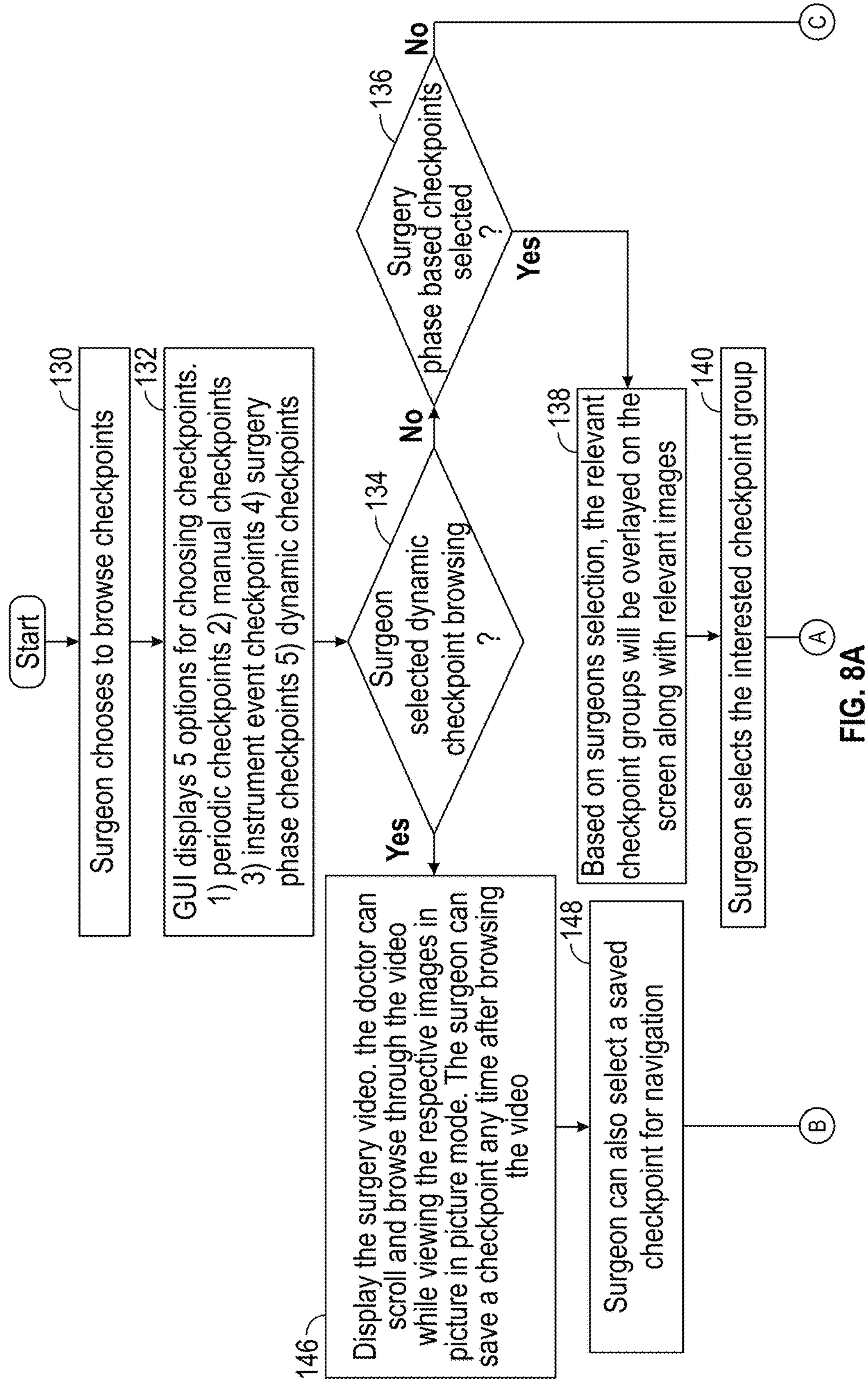
FIGS. 8A and B each show a flow chart of a method for restoring checkpoints according to an embodiment of the present disclosure.
Figure 8A:
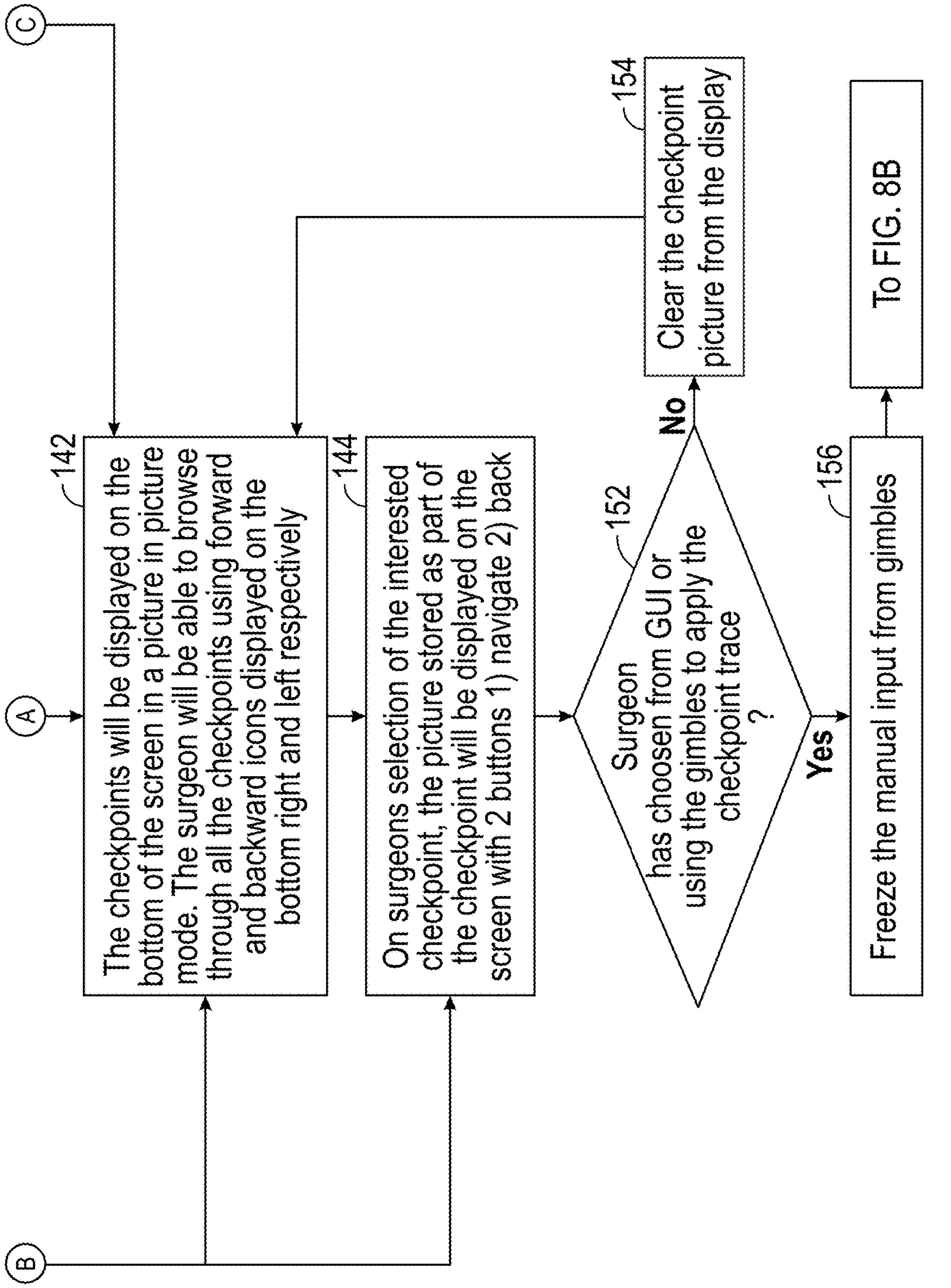
Figure 8B:
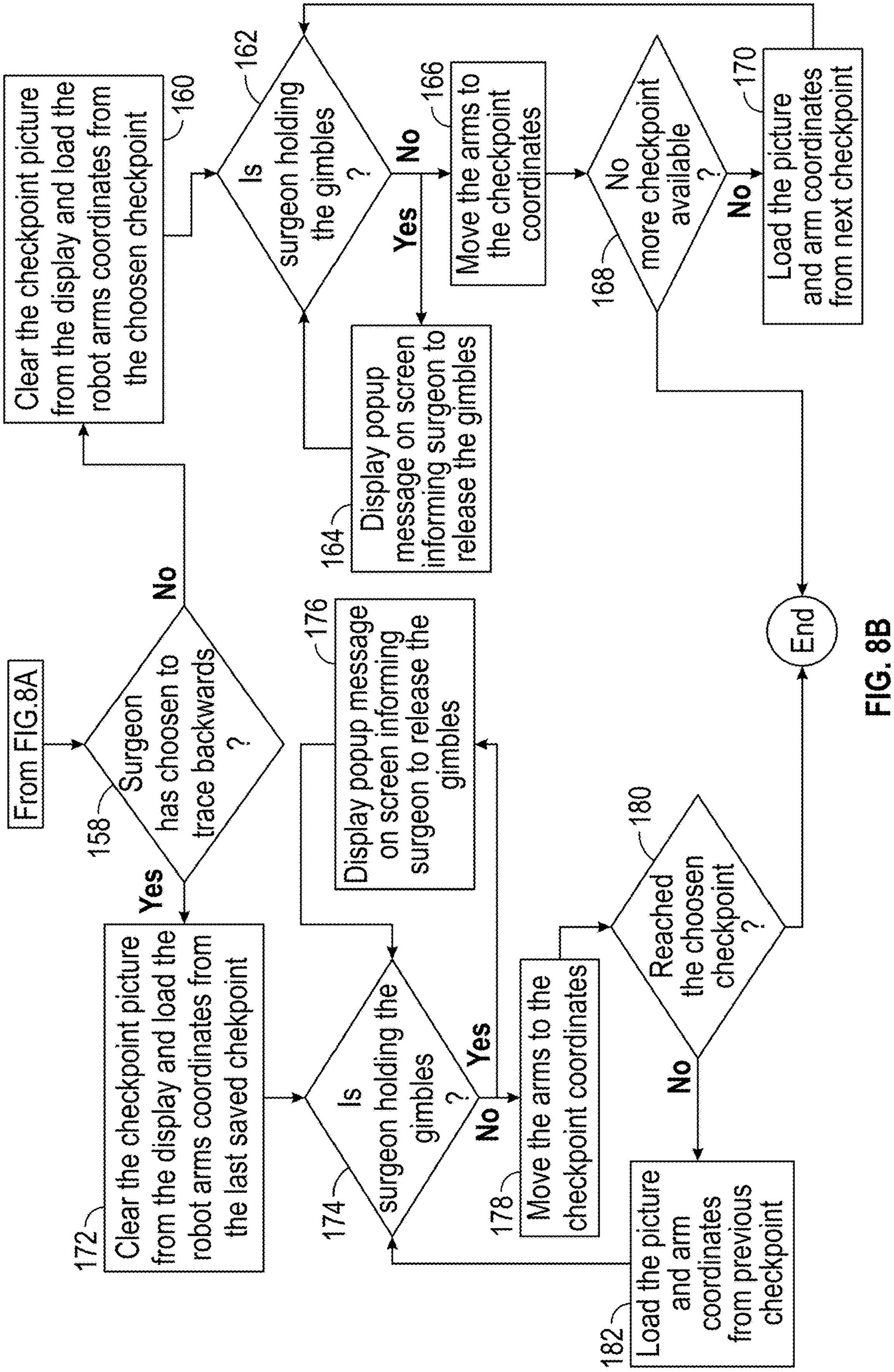
Figure 9:
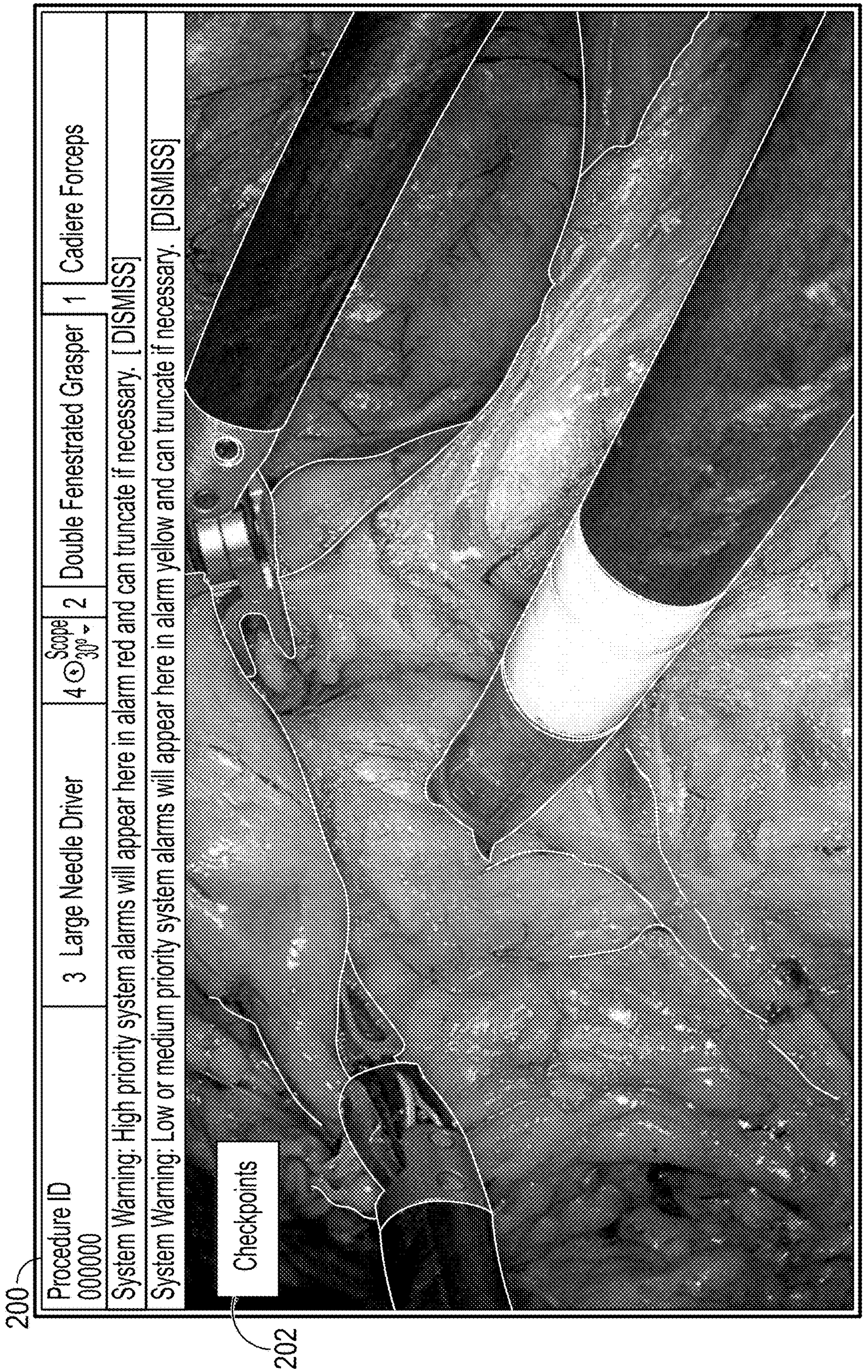
FIGS. 9-20 are screenshots of a graphical user interface (GUI) implementing the methods of FIGS. 7 and 8 according to an embodiment of the present disclosure.
Figure 10:
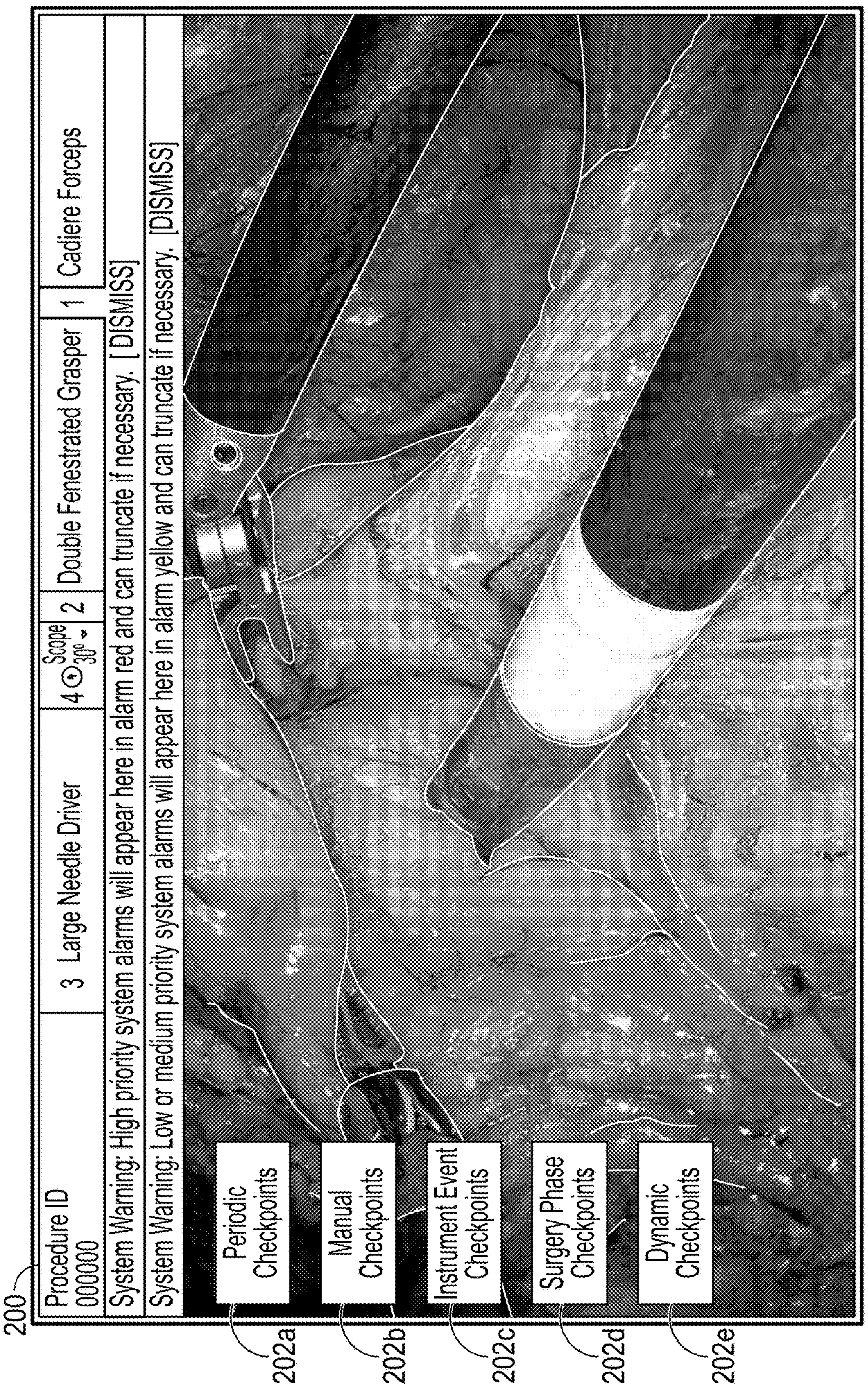

FIGS. 8A and 8B show a method for restoring the checkpoints for the robotic arm 40 controlling the camera 51. The method may be implemented as software instructions executable by the controller 21*a* or any other suitable processor of the system 10. While the method is described with respect to restoring the camera 51 and its corresponding robotic arm 40 to a selected checkpoint, the method may be also extended to control other robotic arms 40 and their instruments 50.

The surgeon or the staff may browse and restore any desired checkpoint using the GUI 200 of FIGS. 9-20, which is displayed as an overlay on the screen 32 of the surgeon console 30 or any other suitable screen of the system 10. The screen 32 may overlay the GUI 200 over the video feed from the camera 51 or as a separate menu screen. At step 130, the user activates the GUI 200 by pressing a checkpoints button 202 via any suitable input method (e.g., touch input, pointer, etc.)

At step 132, once pressed, the GUI 200 displays multiple types of checkpoints that have been previously saved. Exemplary categories include, but are not limited to, periodic checkpoints saved during step 118, manual checkpoints saved during step 120, instrument event check points saved during the step 116, phase checkpoints saved during step 114, and dynamic checkpoints. Each category is further accessible via its own button 202*a-e*, respectively.

Figure 15:
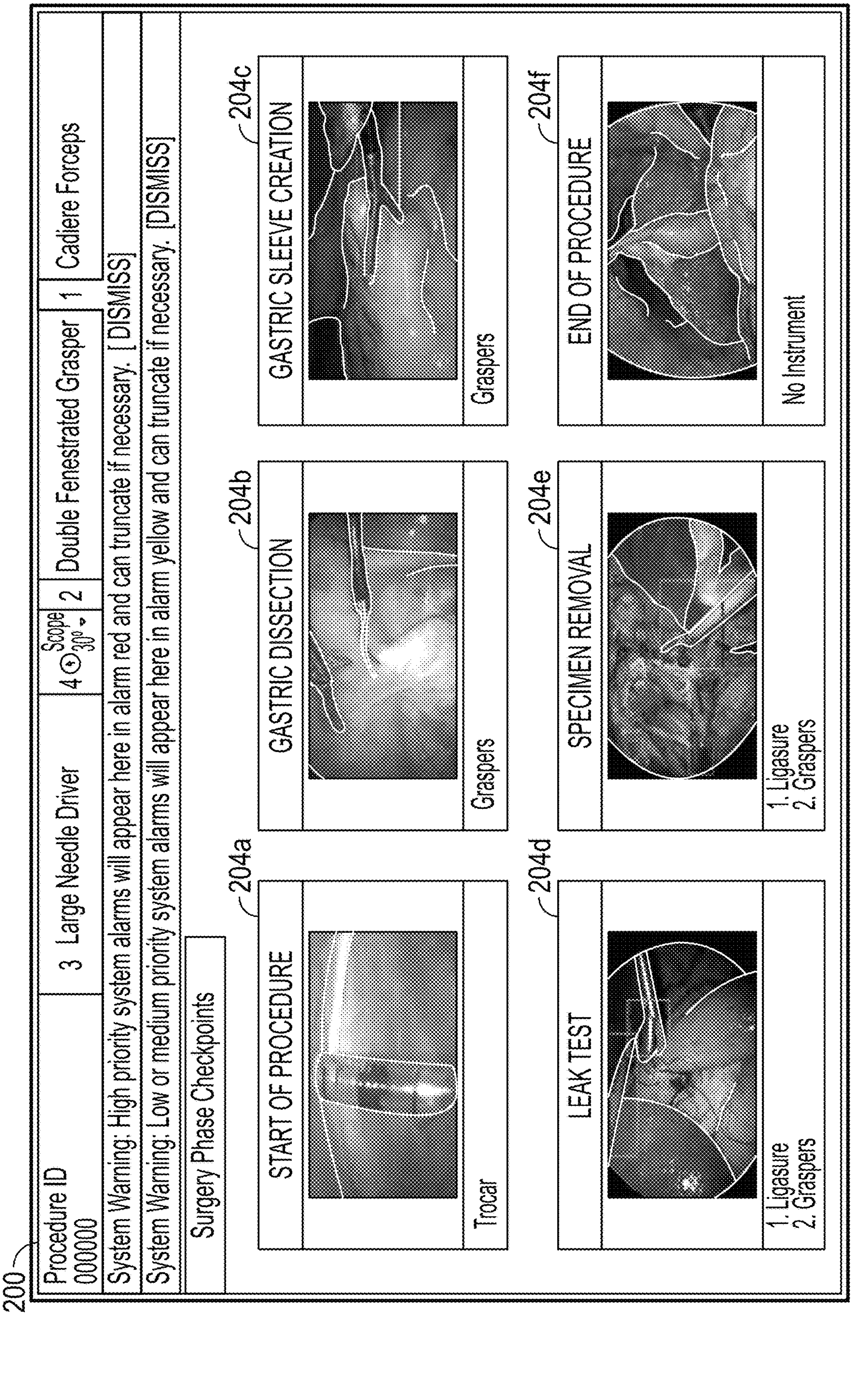

At step 134, the controller 21*a* receives the input selecting one of the buttons 202*a-d*. If the selected input is not the dynamic checkpoint option via the button 202*e*, then the controller 21*a* checks whether the selected input is for phase checkpoints selected via the button 202*d*. If yes, then the controller proceeds to step 138 during which the saved phase checkpoint groups 204*a-f* are displayed (e.g., overlayed) on the GUI 200 as shown in FIG. 15. Each of the groups 204*a-f* may be represented by an image (i.e., thumbnail screenshot) of the video corresponding to the checkpoint group and list affected instruments 50 and/or the camera 51. At step 140, the user selects which of the checkpoint groups 204*a-f* to display the checkpoints captured during the phase. Each of the checkpoint groups may include one or more checkpoints.

Figure 11:
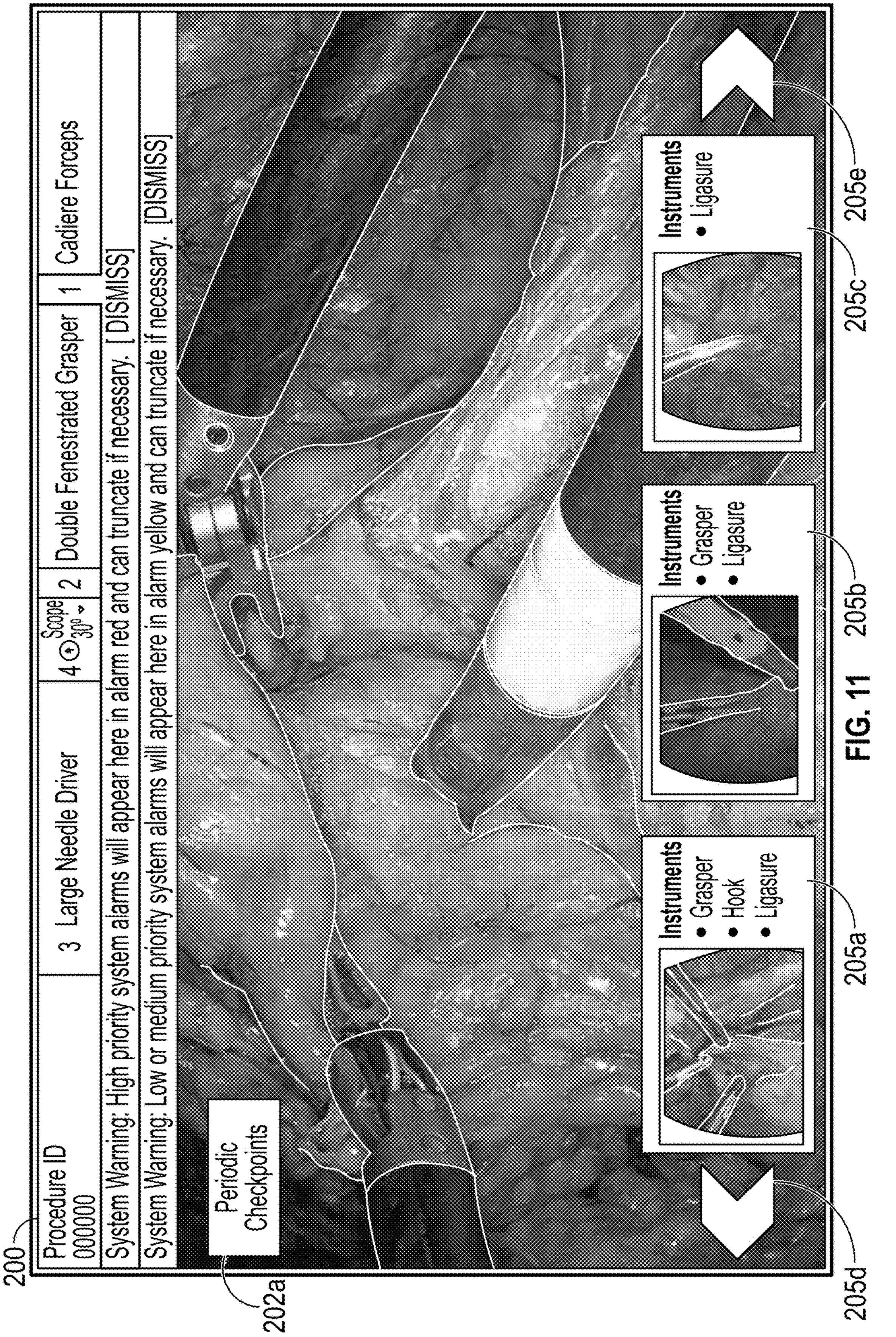
Figure 12:
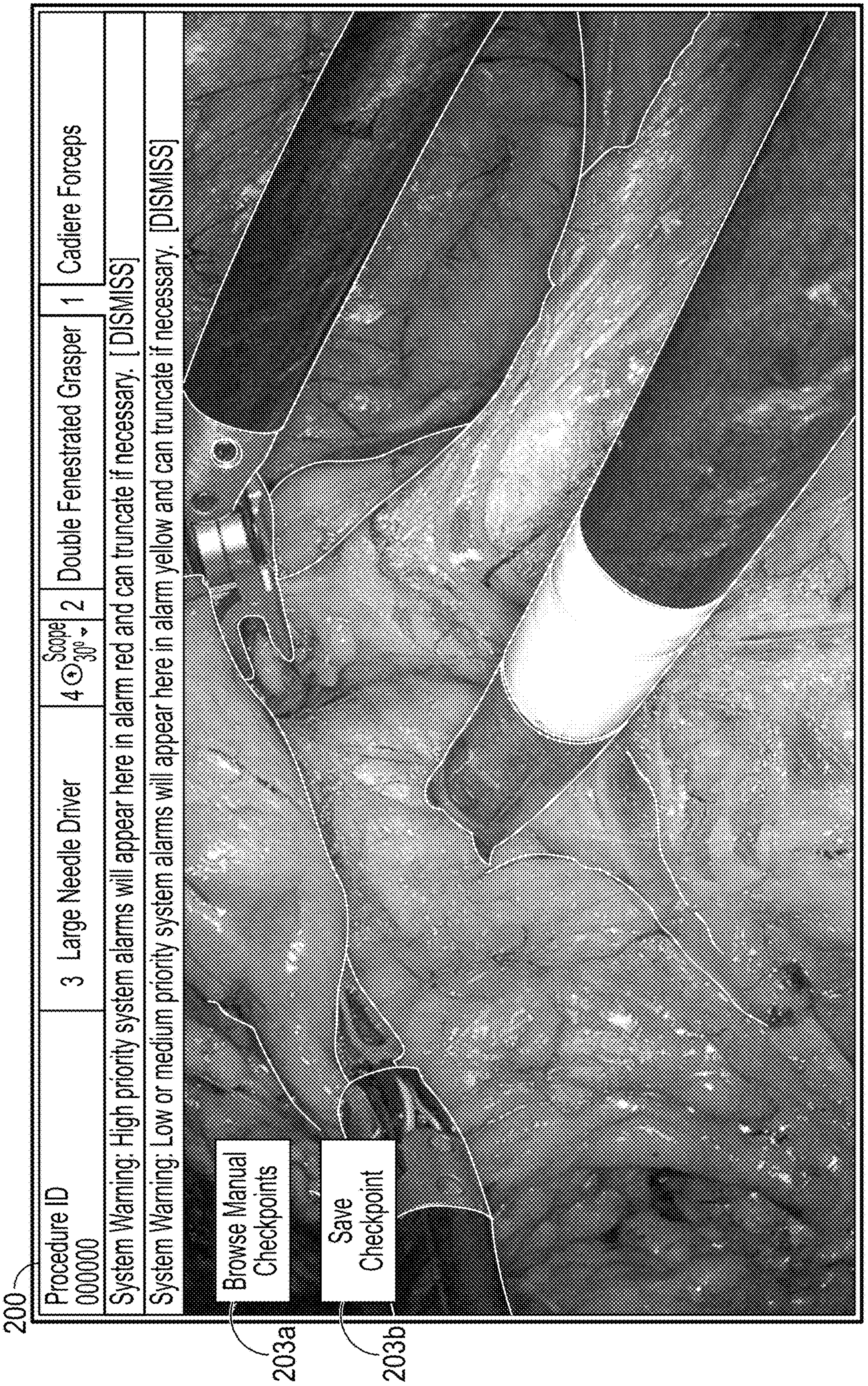
Figure 13:
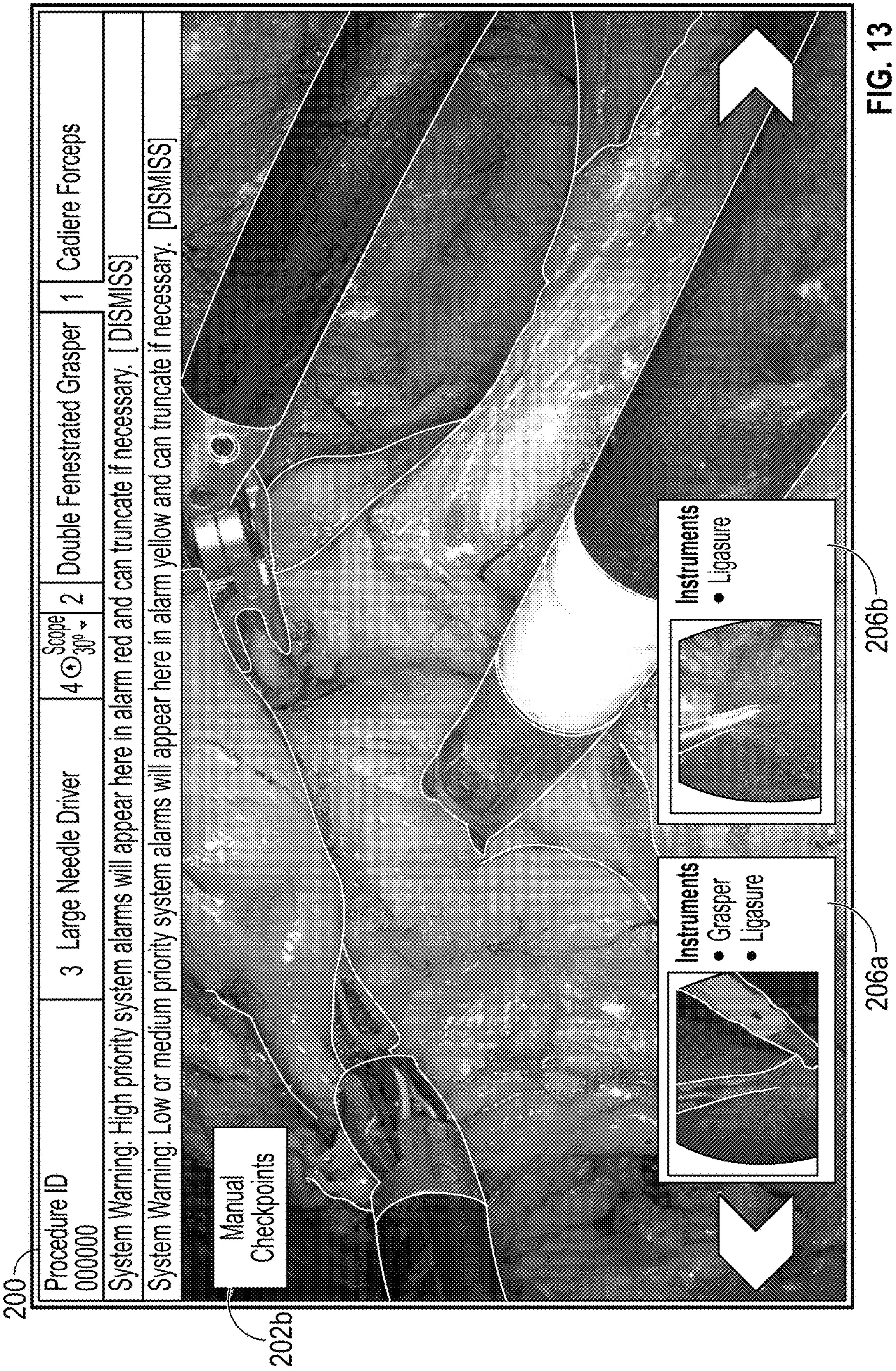
Figure 14:
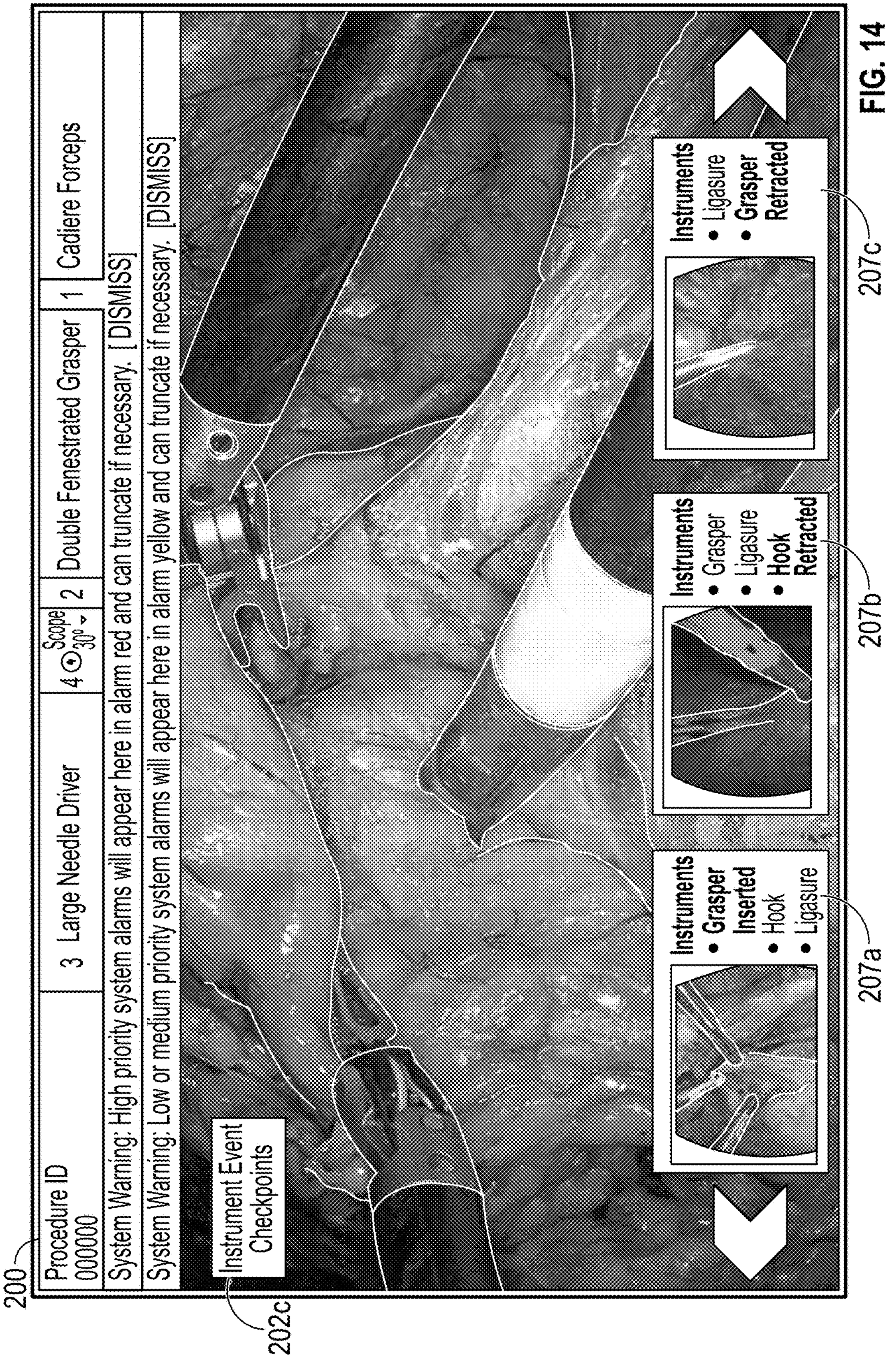

Returning to step 136, if the selected button is one of buttons 202*a-c*, selecting periodic, manual, or instrument checkpoints, respectively, then the controller proceeds to step 142 during which the user selects one or more associated checkpoints as shown in FIGS. 11, 13, and 14.

FIG. 11 shows periodic checkpoints 205*a-c*, which are displayed as a submenu of the periodic checkpoints button 202*a*. Each checkpoint 205*a-c* may be represented by an image (i.e., thumbnail screenshot) of the video corresponding to the checkpoint and list affected instruments 50 and/or the camera 51. The GUI 200 may include arrows 205*d* and 205*e* for scrolling through additional checkpoints. FIG. 13 shows manual checkpoints 206*a* and 206*b*, which are displayed as a submenu of the manual checkpoints button 202*b*. FIG. 14 shows instrument checkpoints 207-*c*, which are displayed as a submenu of the manual checkpoints button 202*c*.

Figure 16:
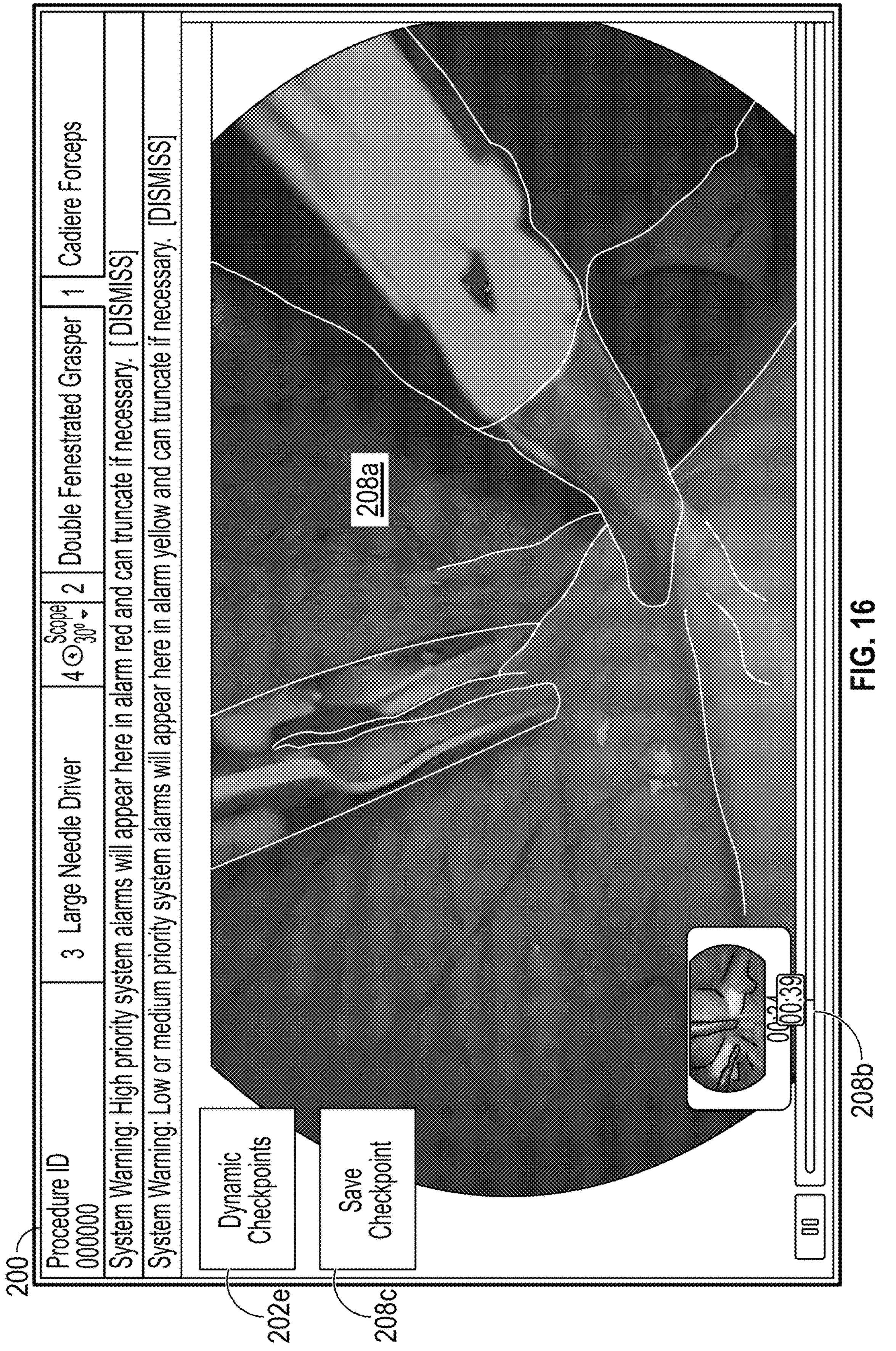
Figure 17:

Returning to step 134, if the user selects button 202*e* then dynamic checkpoint selection is enabled at step 146 as shown in FIGS. 16 and 17. The dynamic checkpoint selection includes a video stream 208*a* of the entire procedure or a portion thereof as well as playback controls 208*b* allowing the user to jump to a desired point and select a dynamic checkpoint via a button 208*c*. The video steam 208*a* may be displayed in any manner, e.g., picture-in-picture mode or overlayed over the video feed of the camera 51. At step 148, the user can also select a previously saved dynamic checkpoint.

Figure 18:
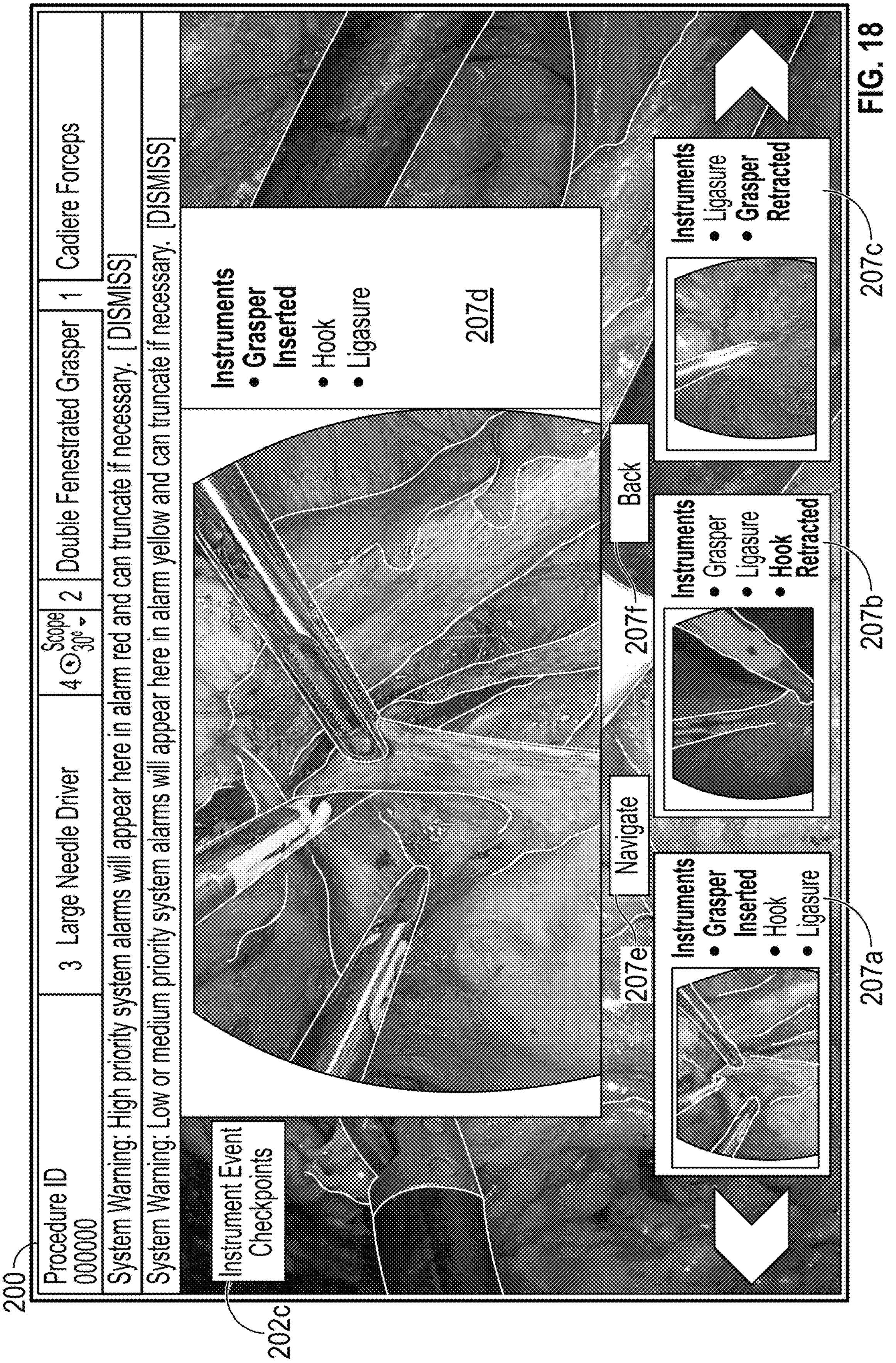
Figure 19:
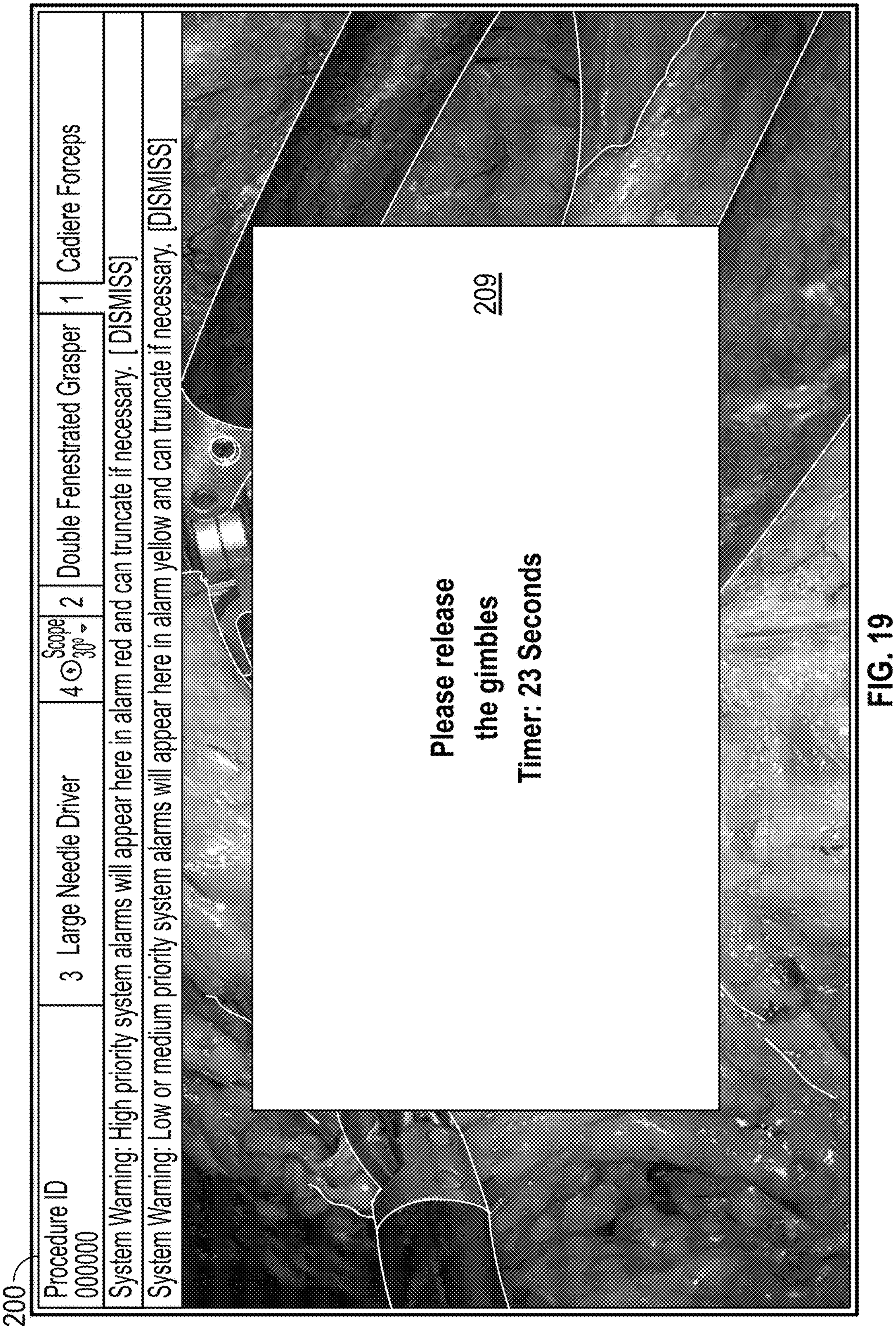

Once the user selects a checkpoint, checkpoint navigation is enabled at step 144. FIG. 18 shows when one of the checkpoints 207*a-c* or any other checkpoints described above is selected. The selected checkpoint, i.e., checkpoint 207*a*, is enlarged as window 207*d* as well as a navigation button 207*e* and a back button 207*f* to revert to checkpoint selection. At step 152, the controller 21*a* checks which button 207*e* or 207*f* was pressed. Pressing button 207*f* removes the enlarged window 207*d* at step 154 and returns the GUI 200 back to step 142 where the available checkpoints for a given submenu (i.e., manual, instrument, period, phase, etc.) are shown. Pressing the navigate button 207*e* freezes input from the gimbals of the handle controllers 38*a* and 38*b* at step 156, in preparation for navigating through the selected checkpoint. Each of the handle controllers 38*a* and 38*b* include a gimbal assembly (not shown) allowing for movement and rotation of the handle controllers 38*a* and 38*b* about three axes (x, y, z). Details of the handle controllers 38*a* and 38*b*, including gimbal operation, are provided in U.S. Patent Application Publication No. 2020/0315729, titled "Control arm assemblies for robotic surgical systems" filed on Nov. 30, 2018, the entire contents of which are incorporated by reference herein.

At step 158, the controller 21*a* checks whether the user selected to navigate backwards or forward through the selected checkpoint. If the user selected to navigate forward, then at step 160 the GUI 200 clears the checkpoint video and/or thumbnail. The controller 21*a* also loads from storage 22*a* coordinates or other data (e.g., kinematics) for placing the robot arms 40*a-d* and their corresponding instruments 50 and/or camera 51 into the position and configuration of the selected checkpoint. In addition to controlling the robotic arms 40*a-d*, individual IDU 52 are also actuated to achieve the desired checkpoint. The forward navigation may be used during reinsertion of instruments 50 and/or camera 51 after extraction for instrument replacement or cleaning of the camera 51. This allows for the system 10 to quickly resume operation after the interruption caused by removal of the instruments 50 and/or camera 51 from the surgical site.

Figure 20:
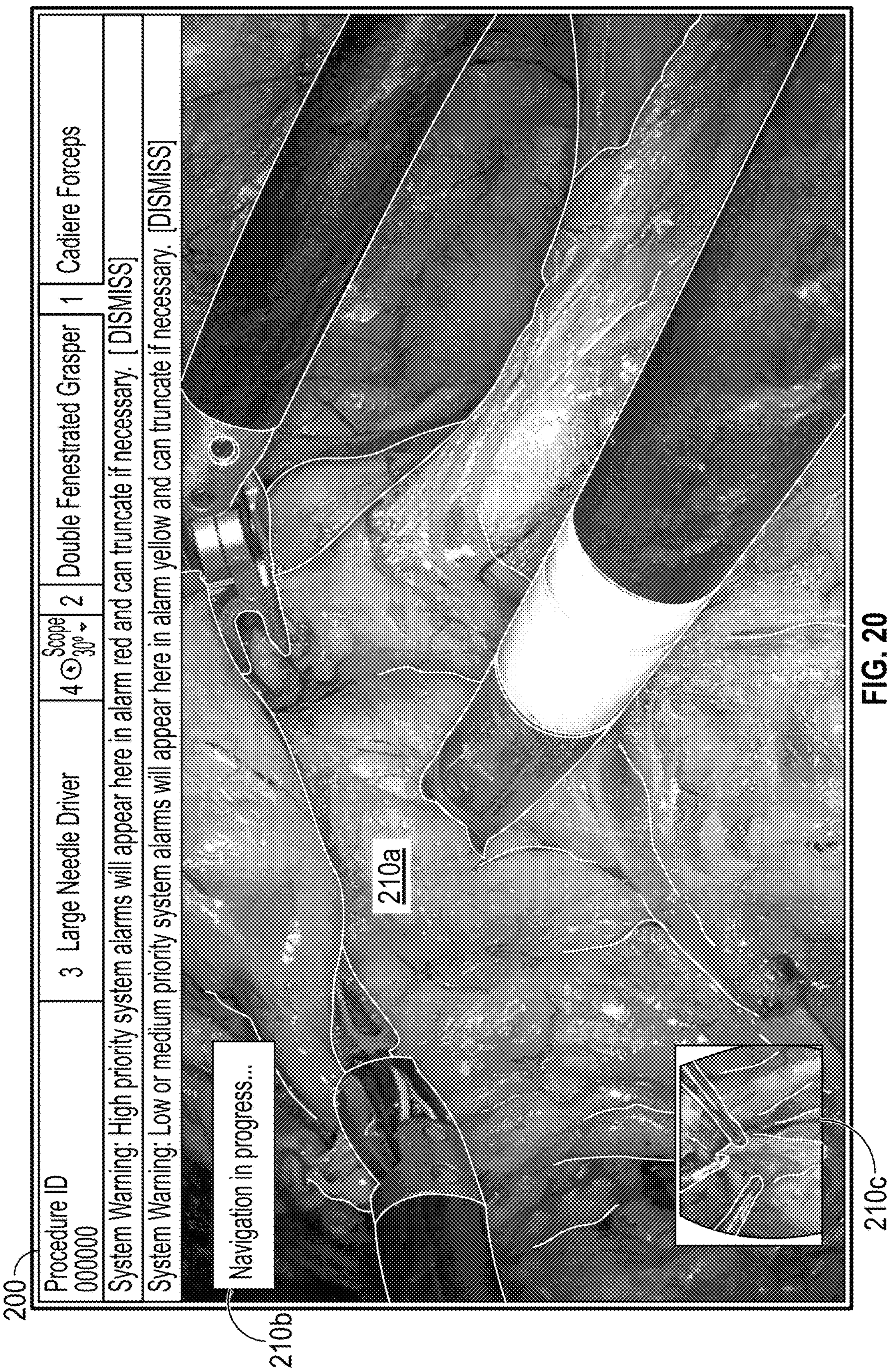

At step 162, the controller 21*a* verifies if the handle controllers 38*a* and 38*b* are being held by the user. If one of the handle controllers 38*a* or 38*b* is being moved, then at step 164 the controller 21*a* displays a prompt 209 to the user to release the handle controllers 38*a* and 38*b*. At step 166, the controller 21*a* automatically moves the robotic arms 40*a-d* and associated instruments 50/camera 51 to the loaded coordinates of the checkpoint. At step 168, the controller 21*a* checks if there are any other checkpoints available that need to be loaded based on the selected forward direction of the navigation. At step 170, the controller 21*a* continues to load subsequent checkpoints until a desired or final checkpoint is reached, i.e., the camera 51 is returned to its position prior inside the patient to its extraction. During navigation, the video feed 210*a* of the camera 51 is shown with a message 210*b* that navigation is in progress as shown in FIG. 20. In addition, the checkpoint to which the system 10 is being restored is shown in a thumbnail 210*c*. This provides the user with visual confirmation that the system 10 has reached the checkpoint, i.e., once the feed 210*a* matches the thumbnail 210*c*.

Returning to step 158, if the user selected to navigate backward, then the GUI 200 clears the checkpoint video and/or thumbnail at step 172 and the controller 21*a* loads from storage 22*a* coordinates or other data (e.g., kinematics) for placing the robot arms 40*a-d* and their corresponding instruments 50 and/or camera 51 into the position and configuration of the selected checkpoint. Backward navigation may be used for extraction of instruments 50 and/or camera 51 for instrument replacement or cleaning of the camera 51.

At step 174, the controller 21*a* verifies if the handle controllers 38*a* and 38*b* are being held by the user. If one of the handle controllers 38*a* or 38*b* is being moved, then at step 176 the controller 21*a* displays a prompt 209 to the user to release the handle controllers 38*a* and 38*b*. At step 178, the controller 21*a* automatically moves the robotic arms 40*a-d* and associated instruments 50/camera 51 to the loaded coordinates of the checkpoint. At step 180, the controller 21*a* checks if there are any other checkpoints available that need to be loaded based on the selected forward direction of the navigation. At step 182, the controller 21*a* continues to load subsequent checkpoints until a desired or final checkpoint is reached, i.e., the camera 51 is returned to its initial position prior to its insertion into the patient. In further embodiments, the controller 21*a* may disable input from the handle controllers 38*a* and 38*b* during the movement of the robotic arms 40*a-d* to the checkpoint position.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:

a surgical robotic arm including a laparoscopic camera and an instrument drive unit configured to actuate the laparoscopic camera;

a surgeon console including a hand controller configured to receive user input to control at least one of the surgical robotic arm or the laparoscopic camera surgical device; and a control tower coupled to the surgical robotic arm and the surgeon console, the control tower including:

a storage device; and a controller configured to:

store a plurality of checkpoints on the storage device, each checkpoint of the plurality of checkpoints including image data of a surgical site and position data corresponding to a prior position of the surgical robotic arm during a surgical procedure, wherein a first checkpoint of the plurality of checkpoints includes position data corresponding to the laparoscopic camera being outside a patient, and wherein a second checkpoint of the plurality of checkpoints includes position data corresponding to the laparoscopic camera being inside the patient;

output a graphical user interface (GUI) on a display screen, the GUI configured to display the image data of at least one checkpoint of the plurality of checkpoints and to receive user input selecting the at least one checkpoint; and in response to receiving the user input selecting the at least one checkpoint:

freeze the user input from the hand controller;

determine whether the hand controller is being held by a user; and after determining that the hand controller is not being held by the user, control the surgical robotic arm to move the laparoscopic camera to the prior position corresponding to the selected at least one checkpoint.

2. The surgical robotic system according to claim 1, wherein the controller is further configured to store the at least one checkpoint of the plurality of checkpoints in response to activation of the laparoscopic camera.

3. The surgical robotic system according to claim 1, wherein the controller is further configured to store the at least one checkpoint of the plurality of checkpoints in response to a user command.

4. The surgical robotic system according to claim 1, wherein the controller is further configured to store the at least one checkpoint of the plurality of checkpoints based on an elapsed time of the surgical procedure.

5. The surgical robotic system according to claim 1, wherein the controller is further configured to detect a phase of the surgical procedure.

6. The surgical robotic system according to claim 5, wherein the controller is further configured to store the at least one checkpoint of the plurality of checkpoints based on the detected phase of the surgical procedure.

7. The surgical robotic system according to claim 1, wherein the controller is further configured to output a prompt to release the hand controller when the hand controller is being held by the user.

8. A method for restoring a positional state of a surgical robotic system, the method comprising:

storing on a storage device a plurality of checkpoints including image data of a surgical site and position data corresponding to a prior position during a surgical procedure of a laparoscopic camera held by a surgical robotic arm, wherein a first checkpoint of the plurality of checkpoints corresponds to a position of the laparoscopic camera being outside a patient and a second checkpoint of the plurality of checkpoints corresponds to a position of the laparoscopic camera being inside the patient;

outputting a graphical user interface (GUI) configured to display on a display screen the image data of the plurality of checkpoints;

receiving a first user input through the GUI selecting at least one of the first checkpoint or the second checkpoint; and in response to receiving the first user input:

freezing user input from a hand controller of a surgeon console;

determining whether the hand controller is being held by a user; and controlling the surgical robotic arm to move the laparoscopic camera to the prior position based on selection of at least one of the first checkpoint or the second checkpoint after determining that the hand controller is not being held by the user.

9. The method according to claim 8, further comprising storing at least one of the first checkpoint or the second checkpoint in response to activation of the laparoscopic camera.

10. The method according to claim 8, further comprising storing at least one of the first checkpoint or the second checkpoint in response to a user command.

11. The method according to claim 8, further comprising storing at least one of the first checkpoint or the second checkpoint based on an elapsed time of the surgical procedure.

12. The method according to claim 8, further comprising:

detecting a phase of the surgical procedure; and storing at least one of the first checkpoint or the second checkpoint based on the detected phase of the surgical procedure.

13. The method according to claim 8, further comprising:

outputting a prompt to release the hand controller when the hand controller is being held by the user.

14. A method for restoring positional state of a surgical robotic system, the method comprising:

storing a plurality of checkpoints on a storage device, each checkpoint of the plurality of checkpoints including image data of a surgical site and position data corresponding to a prior position of a surgical robotic arm during a surgical procedure, wherein the surgical robotic arm includes a laparoscopic camera;

outputting a graphical user interface (GUI) configured to display on a display screen the image data of at least one checkpoint of the plurality of checkpoints;

receiving user input through the GUI selecting the at least one checkpoint; and in response to receiving the user input:

freezing user input from a hand controller of a surgeon console;

determining whether the hand controller is being held by a user; and controlling the surgical robotic arm to move the laparoscopic camera to the prior position based on the selected at least one checkpoint after determining that the hand controller is not being held by the user.

15. The method according to claim 14, further comprising storing the at least one checkpoint of the plurality of checkpoints in response to activation of the laparoscopic camera.

16. The method according to claim 14, further comprising storing the at least one checkpoint of the plurality of checkpoints in response to a user command.

17. The method according to claim 14, further comprising storing the at least one checkpoint of the plurality of checkpoints based on an elapsed time of the surgical procedure.

18. The method according to claim 14, further comprising detecting a phase of the surgical procedure.

19. The method according to claim 18, further comprising storing the at least one checkpoint of the plurality of checkpoints based on the detected phase of the surgical procedure.

20. The method according to claim 14, further comprising:

outputting a prompt to release the hand controller when the hand controller is being held by the user.

* * * * *